United States Patent
Silvestrini et al.

(10) Patent No.: US 10,842,616 B2
(45) Date of Patent: Nov. 24, 2020

(54) ACCOMMODATING INTRAOCULAR LENS DEVICE

(71) Applicant: LensGen, Inc., Irvine, CA (US)

(72) Inventors: Thomas Silvestrini, Alamo, CA (US); Daniel Brady, San Juan Capistrano, CA (US); Ramgopal Rao, Irvine, CA (US)

(73) Assignee: LensGen, Inc., Irvine, CA (US)

( * ) Notice: Subject to any disclaimer, the term of this patent is extended or adjusted under 35 U.S.C. 154(b) by 374 days.

(21) Appl. No.: 15/144,568

(22) Filed: May 2, 2016

(65) Prior Publication Data
US 2016/0317287 A1 Nov. 3, 2016

Related U.S. Application Data

(63) Continuation of application No. PCT/US2014/063473, filed on Oct. 31, 2014.
(Continued)

(51) Int. Cl.
*A61F 2/16* (2006.01)

(52) U.S. Cl.
CPC .......... *A61F 2/1635* (2013.01); *A61F 2/1601* (2015.04); *A61F 2/1648* (2013.01);
(Continued)

(58) Field of Classification Search
None
See application file for complete search history.

(56) References Cited

U.S. PATENT DOCUMENTS

| 4,032,502 A | 6/1977 | Lee et al. |
| 4,373,218 A | 2/1983 | Schachar |

(Continued)

FOREIGN PATENT DOCUMENTS

| DE | 20 2010 003217 U1 | 8/2011 |
| EP | 0356050 A1 | 2/1990 |

(Continued)

OTHER PUBLICATIONS

Ehrmann, et al., "Biomechanical analysis of the accommodative apparatus in primates", Clinical and Experimental Optometry, May 2008, vol. 91, Issue 3, pp. 302-312.
(Continued)

*Primary Examiner* — Leslie Lopez
(74) *Attorney, Agent, or Firm* — Knobbe, Martens, Olson & Bear LLP

(57) ABSTRACT

An intraocular lens (IOL) device comprising a first lens, a second lens and a circumferential haptic. The first lens comprises a pair of opposing and deformable surfaces and a cavity defined therebetween. The first lens has a first lens diameter. The second lens has a second lens diameter. The circumferential haptic has an outer peripheral edge and couples the first lens and the second lens. A main IOL cavity is defined by the circumferential haptic, the first lens and the second lens. The IOL device is resiliently biased to an unaccommodated state, characterized by the IOL device having a first diameter $d_1$ in the absence of radial compressive forces exerted on the outer peripheral edge. The IOL device actuates to an accommodated state being characterized by a second diameter $d_2$ in response to radial compressive forces exerted on the outer peripheral edge, wherein $d_1 > d_2$.

28 Claims, 12 Drawing Sheets

Related U.S. Application Data

(60) Provisional application No. 61/899,106, filed on Nov. 1, 2013.

(52) U.S. Cl.
CPC . *A61F 2002/169* (2015.04); *A61F 2002/1682* (2015.04); *A61F 2250/0003* (2013.01)

(56) References Cited

U.S. PATENT DOCUMENTS

| | | |
|---|---|---|
| 4,512,040 A | 4/1985 | McClure |
| 4,585,457 A | 4/1986 | Kalb |
| 4,676,791 A | 6/1987 | LeMaster et al. |
| 4,720,286 A | 1/1988 | Bailey et al. |
| 4,731,078 A | 3/1988 | Stoy et al. |
| 4,822,360 A | 4/1989 | Deacon |
| 4,842,601 A | 6/1989 | Smith |
| 4,882,368 A | 11/1989 | Elias et al. |
| 4,888,012 A | 12/1989 | Horn et al. |
| 4,892,543 A | 1/1990 | Turley |
| 4,932,966 A | 7/1990 | Christie et al. |
| 5,035,710 A | 7/1991 | Nakada et al. |
| 5,059,668 A | 10/1991 | Fukuda et al. |
| 5,074,876 A | 12/1991 | Kelman |
| 5,091,121 A | 2/1992 | Nakada et al. |
| 5,152,788 A | 10/1992 | Isaacson et al. |
| 5,167,883 A | 12/1992 | Takemasa et al. |
| 5,171,773 A | 12/1992 | Chaffe et al. |
| 5,227,447 A | 7/1993 | Sato et al. |
| 5,236,970 A | 8/1993 | Christ et al. |
| 5,264,522 A | 11/1993 | Mize et al. |
| 5,275,623 A | 1/1994 | Sarfarazi |
| 5,278,258 A | 1/1994 | Gerace et al. |
| 5,312,860 A | 5/1994 | Mize et al. |
| 5,326,506 A | 7/1994 | Vanderbilt |
| 5,336,487 A | 8/1994 | Refojo et al. |
| 5,443,506 A | 8/1995 | Garabet |
| 5,447,987 A | 9/1995 | Sato et al. |
| 5,489,302 A | 2/1996 | Skottun |
| 5,583,178 A | 12/1996 | Oxman et al. |
| 5,607,472 A | 3/1997 | Thompson |
| 5,665,794 A | 9/1997 | Maxson et al. |
| 5,854,310 A | 12/1998 | Maxson |
| 6,071,439 A | 6/2000 | Bawa et al. |
| 6,117,171 A | 9/2000 | Skottun |
| 6,361,561 B1 | 3/2002 | Huo et al. |
| 6,551,354 B1 | 4/2003 | Ghazizadeh et al. |
| 6,616,691 B1 | 9/2003 | Tran |
| 6,695,881 B2 | 2/2004 | Peng et al. |
| 6,730,123 B1 | 5/2004 | Klopotek |
| 6,836,374 B2 | 12/2004 | Esch et al. |
| 6,855,164 B2 | 2/2005 | Glazier |
| 6,858,040 B2 | 2/2005 | Nguyen et al. |
| 6,860,601 B2 | 3/2005 | Shadduck |
| 6,926,736 B2 | 8/2005 | Peng et al. |
| 6,930,838 B2 | 8/2005 | Schachar |
| 6,935,743 B2 | 8/2005 | Shadduck |
| 6,966,649 B2 | 11/2005 | Shadduck |
| 6,969,403 B2 | 11/2005 | Peng et al. |
| 7,041,134 B2 | 5/2006 | Nguyen et al. |
| 7,063,723 B2 | 6/2006 | Ran |
| 7,068,439 B2 | 6/2006 | Esch et al. |
| 7,122,053 B2 | 10/2006 | Esch |
| 7,150,760 B2 | 12/2006 | Zhang |
| 7,217,288 B2 | 5/2007 | Esch et al. |
| 7,220,279 B2 | 5/2007 | Nun |
| 7,223,288 B2 | 5/2007 | Zhang et al. |
| 7,226,478 B2 | 6/2007 | Ting et al. |
| 7,229,475 B2 | 6/2007 | Glazier |
| 7,238,201 B2 | 7/2007 | Portney et al. |
| 7,247,168 B2 | 7/2007 | Esch et al. |
| 7,261,737 B2 | 8/2007 | Esch et al. |
| 7,264,351 B2 | 9/2007 | Shadduck |
| 7,276,619 B2 | 10/2007 | Kunzler et al. |
| 7,278,739 B2 | 10/2007 | Shadduck |
| 7,316,713 B2 | 1/2008 | Zhang |
| 7,416,562 B2 | 8/2008 | Gross |
| 7,438,723 B2 | 10/2008 | Esch |
| 7,452,377 B2 | 11/2008 | Watling et al. |
| 7,453,646 B2 | 11/2008 | Lo |
| 7,485,144 B2 | 2/2009 | Esch |
| 7,591,849 B2 | 9/2009 | Richardson |
| 7,637,947 B2 | 12/2009 | Smith et al. |
| 7,662,179 B2 | 2/2010 | Sarfarazi |
| 7,675,686 B2 | 3/2010 | Lo et al. |
| 7,753,953 B1 | 7/2010 | Yee |
| 7,776,088 B2 | 8/2010 | Shadduck |
| 7,780,729 B2 | 8/2010 | Nguyen et al. |
| 7,815,678 B2 | 10/2010 | Nun |
| 7,842,087 B2 | 11/2010 | Nun |
| 7,854,764 B2 | 12/2010 | Nun |
| 7,857,850 B2 | 12/2010 | Mentak et al. |
| 7,981,155 B2 | 7/2011 | Cumming |
| 7,985,253 B2 | 7/2011 | Cumming |
| 7,986,465 B1 | 7/2011 | Lo et al. |
| 7,998,198 B2 | 8/2011 | Angelopoulos et al. |
| 7,998,199 B2 | 8/2011 | Nun |
| 8,012,204 B2 | 9/2011 | Weinschenk, III et al. |
| 8,018,658 B2 | 9/2011 | Lo |
| 8,034,106 B2 | 10/2011 | Mentak et al. |
| 8,034,107 B2 | 10/2011 | Stenger |
| 8,038,711 B2 | 10/2011 | Clarke |
| 8,048,155 B2 | 11/2011 | Shadduck |
| 8,052,752 B2 | 11/2011 | Woods et al. |
| 8,062,361 B2 | 11/2011 | Nguyen et al. |
| 8,070,806 B2 | 12/2011 | Khoury |
| 8,158,712 B2 | 4/2012 | Your |
| 8,182,531 B2 | 5/2012 | Hermans et al. |
| 8,187,325 B2 | 5/2012 | Zadno-Azizi et al. |
| 8,197,541 B2 | 6/2012 | Schedler |
| 8,216,306 B2 | 7/2012 | Coroneo |
| 8,246,679 B2 | 8/2012 | Nguyen et al. |
| 8,254,034 B1 | 8/2012 | Shields et al. |
| 8,257,827 B1 | 9/2012 | Shi et al. |
| 8,273,123 B2 | 9/2012 | Nun |
| 8,303,656 B2 | 11/2012 | Shadduck |
| 8,314,927 B2 | 11/2012 | Choi et al. |
| 8,320,049 B2 | 11/2012 | Huang et al. |
| 8,328,869 B2 | 12/2012 | Smiley et al. |
| 8,361,145 B2 | 1/2013 | Scholl et al. |
| 8,377,124 B2 | 2/2013 | Hong et al. |
| 8,398,709 B2 | 3/2013 | Nun |
| 8,414,646 B2 | 4/2013 | De Juan, Jr. et al. |
| 8,425,597 B2 | 4/2013 | Glick et al. |
| 8,425,599 B2 | 4/2013 | Shadduck |
| 8,430,928 B2 | 4/2013 | Liao |
| 8,447,086 B2 | 5/2013 | Hildebrand et al. |
| 8,454,688 B2 | 6/2013 | Esch et al. |
| 8,475,529 B2 | 7/2013 | Clarke |
| 8,496,701 B2 | 7/2013 | Hermans et al. |
| 8,500,806 B1 | 8/2013 | Phillips |
| 8,545,556 B2 | 10/2013 | Woods et al. |
| 8,579,972 B2 | 11/2013 | Rombach |
| 8,585,758 B2 | 11/2013 | Woods |
| 8,608,799 B2 | 12/2013 | Blake |
| 8,608,800 B2 | 12/2013 | Portney |
| 8,613,766 B2 | 12/2013 | Richardson et al. |
| 8,647,384 B2 | 2/2014 | Lu |
| 8,657,878 B2 | 2/2014 | Mentak et al. |
| 8,668,734 B2 | 3/2014 | Hildebrand et al. |
| 8,690,942 B2 | 3/2014 | Hildebrand et al. |
| 8,715,345 B2 | 5/2014 | DeBoer et al. |
| 8,715,346 B2 | 5/2014 | De Juan, Jr. et al. |
| 8,734,509 B2 | 5/2014 | Mentak et al. |
| 8,771,347 B2 | 7/2014 | DeBoer et al. |
| 8,814,934 B2 | 8/2014 | Geraghty et al. |
| 8,834,565 B2 | 9/2014 | Nun |
| 8,858,626 B2 | 10/2014 | Noy |
| 8,867,141 B2 | 10/2014 | Pugh et al. |
| 8,900,298 B2 | 12/2014 | Anvar et al. |
| 8,900,300 B1 | 12/2014 | Wortz |
| 8,956,408 B2 | 2/2015 | Smiley et al. |
| 8,968,396 B2 | 3/2015 | Matthews et al. |
| 8,968,399 B2 | 3/2015 | Ghabra |

(56) References Cited

U.S. PATENT DOCUMENTS

| | | |
|---|---|---|
| 8,992,609 B2 | 3/2015 | Shadduck |
| 9,005,282 B2 | 4/2015 | Chang et al. |
| 9,005,283 B2 | 4/2015 | Nguyen et al. |
| 9,034,035 B2 | 5/2015 | Betser et al. |
| 9,044,317 B2 | 6/2015 | Hildebrand et al. |
| 9,072,600 B2 | 7/2015 | Tran |
| 9,090,033 B2 | 7/2015 | Carson et al. |
| 9,095,424 B2 | 8/2015 | Kahook et al. |
| 9,125,736 B2 | 9/2015 | Kahook et al. |
| 9,186,244 B2 | 11/2015 | Silvestrini et al. |
| 9,198,752 B2 | 12/2015 | Woods |
| 9,277,987 B2 | 3/2016 | Smiley et al. |
| 9,277,988 B1 | 3/2016 | Chu |
| 9,289,287 B2 | 3/2016 | Kahook et al. |
| 9,326,846 B2 | 5/2016 | Devita Gerardi et al. |
| 9,333,072 B2 | 5/2016 | Ichikawa |
| 9,358,103 B1 | 6/2016 | Wortz et al. |
| 9,364,316 B1 | 6/2016 | Kahook et al. |
| 9,387,069 B2 | 7/2016 | Kahook et al. |
| 9,421,088 B1 | 8/2016 | Kahook et al. |
| 9,427,312 B2 | 8/2016 | DeBoer et al. |
| 9,433,497 B2 | 9/2016 | DeBoer et al. |
| 9,456,895 B2 | 10/2016 | Shadduck |
| 9,486,311 B2 | 11/2016 | Argento et al. |
| 9,610,155 B2 | 4/2017 | Matthews |
| 9,622,852 B2 | 4/2017 | Simonov et al. |
| 9,629,712 B2 | 4/2017 | Stenger |
| 9,636,213 B2 | 5/2017 | Brady |
| 9,655,716 B2 | 5/2017 | Cumming |
| 9,681,946 B2 | 6/2017 | Kahook et al. |
| 9,693,858 B2 | 7/2017 | Hildebrand et al. |
| 9,713,526 B2 | 7/2017 | Rombach |
| 9,713,527 B2 | 7/2017 | Nishi et al. |
| 9,717,589 B2 | 8/2017 | Simonov et al. |
| 9,744,027 B2 | 8/2017 | Jansen |
| 9,744,028 B2 | 8/2017 | Simonov et al. |
| 9,795,473 B2 | 10/2017 | Smiley et al. |
| 9,808,339 B2 | 11/2017 | Dorronsoro Diaz et al. |
| 9,814,568 B2 | 11/2017 | Ben Nun |
| 9,814,570 B2 | 11/2017 | Robert et al. |
| 9,820,849 B2 | 11/2017 | Jansen |
| 9,848,980 B2 | 12/2017 | McCafferty |
| 9,855,137 B2 | 1/2018 | Smiley et al. |
| 9,855,139 B2 | 1/2018 | Matthews et al. |
| 9,861,469 B2 | 1/2018 | Simonov et al. |
| 9,872,762 B2 | 1/2018 | Scholl et al. |
| 9,872,763 B2 | 1/2018 | Smiley et al. |
| 9,877,825 B2 | 1/2018 | Kahook et al. |
| 9,883,940 B2 | 2/2018 | Nishi et al. |
| 9,925,039 B2 | 3/2018 | Sohn et al. |
| 9,925,040 B2 | 3/2018 | Kahook et al. |
| 9,931,202 B2 | 4/2018 | Borja et al. |
| 9,987,126 B2 | 6/2018 | Borja et al. |
| 10,004,596 B2 | 6/2018 | Brady et al. |
| 10,028,824 B2 | 7/2018 | Kahook et al. |
| 10,045,844 B2 | 8/2018 | Smiley et al. |
| 10,080,648 B2 | 9/2018 | Kahook et al. |
| 10,111,745 B2 | 10/2018 | Silvestrini et al. |
| 10,159,564 B2 | 12/2018 | Brady et al. |
| 10,195,018 B2 | 2/2019 | Salahieh et al. |
| 10,195,020 B2 | 2/2019 | Matthews |
| 10,526,353 B2 | 1/2020 | Silvestrini |
| 2002/0005344 A1 | 1/2002 | Heidlas et al. |
| 2002/0055776 A1 | 5/2002 | Juan, Jr. et al. |
| 2002/0071856 A1 | 6/2002 | Dillingham et al. |
| 2002/0120329 A1 | 8/2002 | Lang et al. |
| 2003/0093149 A1 | 5/2003 | Glazier |
| 2003/0105522 A1 | 6/2003 | Glazier |
| 2003/0109926 A1 | 6/2003 | Portney |
| 2003/0149480 A1 | 8/2003 | Shadduck |
| 2003/0158295 A1 | 8/2003 | Fukuda et al. |
| 2004/0082993 A1* | 4/2004 | Woods .................. A61F 2/1635 623/6.28 |
| 2004/0082994 A1 | 4/2004 | Woods et al. |
| 2004/0111152 A1 | 6/2004 | Kelman |
| 2004/0111153 A1 | 6/2004 | Woods et al. |
| 2004/0148023 A1 | 7/2004 | Shu |
| 2004/0162612 A1 | 8/2004 | Portney et al. |
| 2004/0169816 A1 | 9/2004 | Esch |
| 2004/0181279 A1 | 9/2004 | Nun |
| 2004/0249455 A1 | 12/2004 | Tran |
| 2005/0021139 A1 | 1/2005 | Shadduck |
| 2005/0071002 A1* | 3/2005 | Glazier .................. A61F 2/1613 623/6.13 |
| 2005/0107873 A1 | 5/2005 | Zhou |
| 2005/0119740 A1 | 6/2005 | Esch et al. |
| 2005/0137703 A1 | 6/2005 | Chen |
| 2005/0251253 A1 | 11/2005 | Gross |
| 2005/0251254 A1 | 11/2005 | Brady et al. |
| 2005/0267575 A1* | 12/2005 | Nguyen .................. A61F 2/1613 623/6.34 |
| 2006/0041307 A1 | 2/2006 | Esch et al. |
| 2006/0047339 A1 | 3/2006 | Brown |
| 2006/0069178 A1 | 3/2006 | Rastogi et al. |
| 2006/0074487 A1 | 4/2006 | Gilg |
| 2006/0100701 A1 | 5/2006 | Esch et al. |
| 2006/0111776 A1 | 5/2006 | Glick et al. |
| 2006/0134173 A1 | 6/2006 | Liu et al. |
| 2006/0135477 A1 | 6/2006 | Haitjema et al. |
| 2006/0155372 A1 | 7/2006 | Coroneo |
| 2006/0212116 A1 | 9/2006 | Woods |
| 2006/0238702 A1 | 10/2006 | Glick et al. |
| 2006/0241752 A1 | 10/2006 | Israel |
| 2007/0010880 A1 | 1/2007 | Esch |
| 2007/0016293 A1 | 1/2007 | Tran |
| 2007/0021831 A1 | 1/2007 | Clarke |
| 2007/0032868 A1 | 2/2007 | Woods et al. |
| 2007/0050024 A1 | 3/2007 | Zhang |
| 2007/0050025 A1 | 3/2007 | Nguyen et al. |
| 2007/0078515 A1 | 4/2007 | Brady et al. |
| 2007/0088433 A1 | 4/2007 | Esch et al. |
| 2007/0100445 A1 | 5/2007 | Shadduck |
| 2007/0106377 A1 | 5/2007 | Smith et al. |
| 2007/0118216 A1 | 5/2007 | Pynson |
| 2007/0129798 A1 | 6/2007 | Chawdhary |
| 2007/0129799 A1 | 6/2007 | Schedler |
| 2007/0129800 A1 | 6/2007 | Cumming |
| 2007/0129801 A1 | 6/2007 | Cumming |
| 2007/0132949 A1* | 6/2007 | Phelan .................. C08F 283/12 351/159.33 |
| 2007/0185574 A1 | 8/2007 | Nun |
| 2007/0203578 A1 | 8/2007 | Scholl et al. |
| 2007/0213817 A1 | 9/2007 | Esch et al. |
| 2007/0244561 A1 | 10/2007 | Nun |
| 2007/0260308 A1 | 11/2007 | Tran |
| 2007/0260310 A1 | 11/2007 | Richardson |
| 2008/0004699 A1 | 1/2008 | Nun |
| 2008/0015689 A1 | 1/2008 | Esch et al. |
| 2008/0033547 A1 | 2/2008 | Chang et al. |
| 2008/0046074 A1 | 2/2008 | Smith et al. |
| 2008/0046075 A1 | 2/2008 | Esch et al. |
| 2008/0046077 A1 | 2/2008 | Cumming |
| 2008/0051886 A1 | 2/2008 | Lin |
| 2008/0154364 A1 | 6/2008 | Richardson et al. |
| 2008/0188930 A1 | 8/2008 | Mentak et al. |
| 2008/0200982 A1 | 8/2008 | Your |
| 2008/0269887 A1 | 10/2008 | Cumming |
| 2008/0300680 A1 | 12/2008 | Nun |
| 2008/0306587 A1 | 12/2008 | Your |
| 2008/0306588 A1 | 12/2008 | Smiley et al. |
| 2008/0306589 A1 | 12/2008 | Donitzky et al. |
| 2009/0005865 A1 | 1/2009 | Smiley et al. |
| 2009/0027661 A1 | 1/2009 | Choi et al. |
| 2009/0043384 A1 | 2/2009 | Niwa et al. |
| 2009/0116118 A1 | 5/2009 | Frazier et al. |
| 2009/0125106 A1 | 5/2009 | Weinschenk, III et al. |
| 2009/0149952 A1 | 6/2009 | Shadduck |
| 2009/0198326 A1 | 8/2009 | Zhou et al. |
| 2009/0204209 A1 | 8/2009 | Tran |
| 2009/0204210 A1 | 8/2009 | Pynson |
| 2009/0264998 A1 | 10/2009 | Mentak et al. |
| 2009/0292355 A1 | 11/2009 | Boyd et al. |
| 2009/0319040 A1 | 12/2009 | Khoury |
| 2010/0004742 A1 | 1/2010 | Cumming |

(56) References Cited

U.S. PATENT DOCUMENTS

| | | |
|---|---|---|
| 2010/0030332 A1 | 2/2010 | Schedler |
| 2010/0055449 A1 | 3/2010 | Ota |
| 2010/0094412 A1 | 4/2010 | Wensrich |
| 2010/0094413 A1 | 4/2010 | Rombach et al. |
| 2010/0121444 A1 | 5/2010 | Nun |
| 2010/0131058 A1 | 5/2010 | Shadduck |
| 2010/0131059 A1 | 5/2010 | Callahan et al. |
| 2010/0179653 A1 | 7/2010 | Argento et al. |
| 2010/0204787 A1 | 8/2010 | Noy |
| 2010/0211169 A1 | 8/2010 | Stanley et al. |
| 2010/0228344 A1 | 9/2010 | Shadduck |
| 2010/0288346 A1 | 9/2010 | Esch |
| 2010/0324672 A1 | 12/2010 | Esch et al. |
| 2010/0324674 A1 | 12/2010 | Brown |
| 2011/0029074 A1 | 2/2011 | Reisin et al. |
| 2011/0071628 A1 | 3/2011 | Gross et al. |
| 2011/0082544 A1 | 4/2011 | Nun |
| 2011/0112636 A1 | 5/2011 | Nun |
| 2011/0118834 A1 | 5/2011 | Lo et al. |
| 2011/0118836 A1 | 5/2011 | Jain |
| 2011/0160852 A1 | 6/2011 | Mentak et al. |
| 2011/0208301 A1 | 8/2011 | Anvar et al. |
| 2011/0224788 A1 | 9/2011 | Webb |
| 2011/0282442 A1 | 11/2011 | Scholl et al. |
| 2011/0288638 A1 | 11/2011 | Smiley et al. |
| 2012/0016473 A1 | 1/2012 | Brady et al. |
| 2012/0035724 A1 | 2/2012 | Clarke |
| 2012/0071972 A1 | 3/2012 | Zhao |
| 2012/0078361 A1 | 3/2012 | Shadduck |
| 2012/0078364 A1 | 3/2012 | Stenger |
| 2012/0095125 A1 | 4/2012 | Hu et al. |
| 2012/0150292 A1 | 6/2012 | Mentak et al. |
| 2012/0232649 A1* | 9/2012 | Cuevas ............... A61L 27/3869 623/6.16 |
| 2012/0245683 A1 | 9/2012 | Christie et al. |
| 2012/0253458 A1 | 10/2012 | Geraghty et al. |
| 2012/0253459 A1 | 10/2012 | Reich et al. |
| 2012/0290084 A1 | 11/2012 | Coroneo |
| 2012/0296423 A1 | 11/2012 | Caffey |
| 2012/0296424 A1 | 11/2012 | Betser |
| 2012/0310341 A1 | 12/2012 | Simonov et al. |
| 2012/0310343 A1 | 12/2012 | Van Noy |
| 2013/0006353 A1 | 1/2013 | Betser et al. |
| 2013/0018461 A1 | 1/2013 | Nun |
| 2013/0035760 A1 | 2/2013 | Portney |
| 2013/0038944 A1 | 2/2013 | Chang et al. |
| 2013/0060331 A1 | 3/2013 | Shadduck |
| 2013/0110234 A1 | 5/2013 | DeVita et al. |
| 2013/0110235 A1 | 5/2013 | Shweigerling |
| 2013/0116781 A1 | 5/2013 | Nun |
| 2013/0131794 A1 | 5/2013 | Smiley et al. |
| 2013/0190867 A1 | 7/2013 | Peyman |
| 2013/0226295 A1 | 8/2013 | De Juan, Jr. et al. |
| 2013/0231741 A1 | 9/2013 | Clarke |
| 2013/0250239 A1 | 9/2013 | Hildebrand et al. |
| 2013/0268070 A1 | 10/2013 | Esch et al. |
| 2013/0297018 A1 | 11/2013 | Brady et al. |
| 2013/0317607 A1 | 11/2013 | DeBoer et al. |
| 2013/0317608 A1 | 11/2013 | Hermans et al. |
| 2014/0012277 A1 | 1/2014 | Matthews et al. |
| 2014/0058507 A1 | 2/2014 | Reich et al. |
| 2014/0085726 A1 | 3/2014 | Portney |
| 2014/0100654 A1 | 4/2014 | Portney et al. |
| 2014/0107459 A1 | 4/2014 | Lind et al. |
| 2014/0111765 A1 | 4/2014 | DeBoer et al. |
| 2014/0121768 A1 | 5/2014 | Simpson |
| 2014/0135917 A1 | 5/2014 | Glazier |
| 2014/0135918 A1 | 5/2014 | De Juan, Jr. et al. |
| 2014/0142558 A1 | 5/2014 | Culbertson et al. |
| 2014/0172092 A1 | 6/2014 | Carson et al. |
| 2014/0180404 A1 | 6/2014 | Tram |
| 2014/0180405 A1 | 6/2014 | Weinschenk, III et al. |
| 2014/0180406 A1 | 6/2014 | Simpson |
| 2014/0180407 A1 | 6/2014 | Sohn et al. |
| 2014/0180410 A1 | 6/2014 | Gerardi |
| 2014/0227437 A1 | 8/2014 | DeBoer et al. |
| 2014/0228949 A1 | 8/2014 | Argento et al. |
| 2014/0249625 A1 | 9/2014 | Shadduck |
| 2014/0257478 A1 | 9/2014 | McCafferty |
| 2014/0257479 A1 | 9/2014 | McCafferty |
| 2014/0309734 A1 | 10/2014 | Sohn et al. |
| 2015/0087743 A1 | 3/2015 | Anvar et al. |
| 2015/0105760 A1 | 4/2015 | Rao et al. |
| 2015/0127102 A1 | 5/2015 | Wortz |
| 2015/0173892 A1 | 6/2015 | Borja et al. |
| 2015/0202041 A1 | 7/2015 | Shadduck |
| 2015/0216652 A1 | 8/2015 | Jansen |
| 2015/0238310 A1 | 8/2015 | Matthews et al. |
| 2015/0366656 A1 | 12/2015 | Wortz et al. |
| 2016/0000558 A1 | 1/2016 | Honigsbaum |
| 2016/0008126 A1 | 1/2016 | Salahieh et al. |
| 2016/0051361 A1 | 2/2016 | Phillips |
| 2016/0058553 A1 | 3/2016 | Salahieh et al. |
| 2016/0074154 A1 | 3/2016 | Woods |
| 2016/0184089 A1 | 6/2016 | Dudee et al. |
| 2016/0184092 A1 | 6/2016 | Smiley et al. |
| 2016/0208138 A1 | 7/2016 | Nishijima et al. |
| 2016/0256265 A1 | 9/2016 | Borja et al. |
| 2016/0262875 A1 | 9/2016 | Smith et al. |
| 2016/0281019 A1 | 9/2016 | Deklippel et al. |
| 2016/0287380 A1 | 10/2016 | Shi et al. |
| 2017/0020662 A1 | 1/2017 | Shadduck |
| 2017/0049561 A1 | 2/2017 | Smiley et al. |
| 2017/0049562 A1 | 2/2017 | Argento et al. |
| 2017/0216021 A1 | 8/2017 | Brady |
| 2017/0247525 A1 | 8/2017 | Silverstrini et al. |
| 2017/0290658 A1 | 10/2017 | Hildebrand et al. |
| 2017/0319332 A1 | 11/2017 | Kahook et al. |
| 2017/0342096 A1 | 11/2017 | Silvestrini |
| 2017/0348095 A1 | 12/2017 | Wortz et al. |
| 2018/0014928 A1 | 1/2018 | Kahook et al. |
| 2018/0028308 A1 | 2/2018 | Smiley et al. |
| 2018/0110613 A1 | 4/2018 | Wortz et al. |
| 2018/0125640 A1 | 5/2018 | Smiley et al. |
| 2018/0132997 A1 | 5/2018 | Smiley et al. |
| 2018/0147051 A1 | 5/2018 | Scholl et al. |
| 2018/0153682 A1 | 6/2018 | Hajela et al. |
| 2018/0161152 A1 | 6/2018 | Argento et al. |
| 2018/0161153 A1 | 6/2018 | Kahook et al. |
| 2018/0177589 A1 | 6/2018 | Argento et al. |
| 2018/0177639 A1 | 6/2018 | Rao et al. |
| 2018/0256315 A1 | 9/2018 | Hildebrand et al. |
| 2018/0271642 A1 | 9/2018 | Wortz et al. |
| 2018/0271645 A1 | 9/2018 | Brady et al. |
| 2018/0280135 A1 | 10/2018 | Otts |
| 2018/0296323 A1 | 10/2018 | Olcina Portilla |
| 2018/0307061 A1 | 10/2018 | State et al. |
| 2018/0318068 A1 | 11/2018 | Otts et al. |
| 2018/0344453 A1 | 12/2018 | Brady |
| 2018/0368971 A1 | 12/2018 | Zacher et al. |
| 2018/0368973 A1 | 12/2018 | Wortz et al. |
| 2018/0368974 A1 | 12/2018 | Kahook et al. |
| 2019/0000612 A1 | 1/2019 | Rao et al. |
| 2019/0015198 A1 | 1/2019 | Kuiper |
| 2019/0021848 A1 | 1/2019 | Kahook et al. |
| 2019/0069989 A1 | 3/2019 | Otts et al. |
| 2019/0076239 A1 | 3/2019 | Wortz et al. |
| 2019/0076243 A1 | 3/2019 | Hadba et al. |
| 2019/0083235 A1 | 3/2019 | Wortz |
| 2019/0099263 A1 | 4/2019 | Brady et al. |
| 2019/0374334 A1 | 12/2019 | Brady et al. |

FOREIGN PATENT DOCUMENTS

| | | |
|---|---|---|
| EP | 0766540 B1 | 8/1999 |
| EP | 1881818 B1 | 7/2015 |
| JP | H09-150002 A | 6/1997 |
| JP | 2001-525220 | 12/2001 |
| JP | 2005-511201 | 4/2005 |
| JP | 2006-511245 | 4/2006 |
| JP | 2006-516002 | 6/2006 |
| JP | 2010-514507 | 5/2010 |
| JP | 2011-502713 | 1/2011 |
| JP | 2013-047290 | 3/2013 |

(56) References Cited

FOREIGN PATENT DOCUMENTS

| WO | WO 92/17132 | 10/1992 |
|---|---|---|
| WO | WO 99/29266 | 6/1999 |
| WO | WO 2001/034067 | 5/2001 |
| WO | WO 2004/037127 | 5/2004 |
| WO | WO 2004/052242 | 6/2004 |
| WO | WO 2004/054471 | 7/2004 |
| WO | WO 2004/072689 | 8/2004 |
| WO | WO 2006/047383 | 5/2006 |
| WO | WO 2007/005778 | 1/2007 |
| WO | WO 2007/047529 | 4/2007 |
| WO | WO 2007/047530 | 4/2007 |
| WO | WO 2008/024766 | 2/2008 |
| WO | WO 2008/031231 | 3/2008 |
| WO | WO 2008/077040 | 6/2008 |
| WO | WO 2008/082957 | 7/2008 |
| WO | WO 2008/103798 | 8/2008 |
| WO | WO 2009/015161 | 1/2009 |
| WO | WO 2009/015234 | 1/2009 |
| WO | WO 2009/015240 | 1/2009 |
| WO | WO2009015226 A3 | 1/2009 |
| WO | WO 2009/064876 | 5/2009 |
| WO | WO 2010/010565 | 1/2010 |
| WO | WO 2010/081093 | 7/2010 |
| WO | WO 2011/026068 | 3/2011 |
| WO | WO 2011/106435 | 9/2011 |
| WO | WO2011/137191 A1 | 11/2011 |
| WO | WO 2012/006616 | 1/2012 |
| WO | WO 2012/129407 | 9/2012 |
| WO | WO2013016804 A1 | 2/2013 |
| WO | WO 2013/070924 | 5/2013 |
| WO | WO 2013/142323 | 9/2013 |
| WO | WO 2013/166068 | 11/2013 |
| WO | WO 2013/180254 | 12/2013 |
| WO | WO 2013/190130 | 12/2013 |
| WO | WO 2014/099630 | 6/2014 |
| WO | WO 2014/145562 | 9/2014 |
| WO | WO 2014/152017 | 9/2014 |
| WO | WO 2014/197170 | 12/2014 |
| WO | WO 2015/066502 | 5/2015 |
| WO | WO 2015/066532 | 5/2015 |
| WO | WO 2015/126604 | 8/2015 |
| WO | WO 2016/018932 | 2/2016 |
| WO | WO 2016/033217 | 3/2016 |
| WO | WO 2016/122805 | 8/2016 |
| WO | WO 2016/201351 | 12/2016 |
| WO | WO 2017/079449 | 5/2017 |
| WO | WO 2017/079733 | 5/2017 |
| WO | WO 2017/087358 | 5/2017 |
| WO | WO 2017/096087 | 6/2017 |
| WO | WO 2017/192855 | 11/2017 |
| WO | WO 2018/081595 | 5/2018 |
| WO | WO 2018/119408 | 6/2018 |
| WO | WO 2018/167099 | 9/2018 |
| WO | WO 2018/222579 | 12/2018 |
| WO | WO 2018/227014 | 12/2018 |
| WO | WO 2019/005859 | 1/2019 |
| WO | WO 2019/027845 | 2/2019 |

OTHER PUBLICATIONS

Ehrmann, et al., "Ex Vivo Accommodation Simulator II—Concept and Preliminary Results", Proceedings of SPIE vol. 5314, Ophthalmic Technologies XIV, Jul. 2004, pp. 48-58.

Gabel, et al., "Silicone oil with high specific gravity for intraocular use", British Journal of Ophthalmology, Apr. 1987, vol. 71, 262-267.

Ghallagher-Wetmore, et al., "Supercritical fluid processing: a new dry technique for photoresist developing", SPIE's 1995 Symposium on Microlithography, 1995, vol. 2438, 16 pages.

Lane, et al., "Comparison of the biomechanical behavior of foldable intraocular lenses", Journal of Cataract Refract Surg, Nov. 2004, vol. 30, pp. 2397-2402.

Nakamura, et al., "Analysis and Fractionation of Silicone and Fluorosilicone Oils for Intraocular Use", Investigative Ophthalmology & Visual Science, vol. 31, No. 10, Oct. 1990, 2059-2069.

National Center for Biotechnology Information. PubChem Substance Database; SID=184590955, https://pubchem.ncbi.nlm.nih.gov/substance/184590955 (accessed Sep. 20, 2017).

Zhang, et al., "Fluidic adaptive lens with high focal length tunability", Applied Physics Letters, May 2003, vol. 82, No. 19, pp. 3171-3172.

Zhang, et al., "Integrated fluidic adaptive zoom lens", Optics Letters, Dec. 2004, vol. 29, No. 24, pp. 2855-2857.

Zhao, et al., "Strategies for Supercritical $CO_2$ Fractionation of Polydimethylsiloxane," Journal of Applied Polymer Science, 1995, vol. 55, 773-778.

Aliancy, et al., "Long-term capsule clarity with a disk-shaped intraocular lens", Journal of Cataract & Refractive Surgery, Apr. 2018, vol. 44, Issue 4, pp. 504-509.

Kramer, et al., "Prevention of postoperative capsular bag opacification using intraocular lenses and endocapsular devices maintaining an open or expanded capsular bag", Journal of Cataract & Refractive Surgery, Mar. 2016, vol. 42, Issue 3, pp. 469-484.

Leishman, et al., "Prevention of capsular bag opacification with a modified hydrophilic acrylic disk-shaped intraocular lens", Journal of Cataract & Refractive Surgery, Sep. 2012, vol. 38, Issue 9, pp. 1664-1670.

* cited by examiner

ACCOMMODATING INTRAOCULAR LENS DEVICE

CROSS-REFERENCE TO RELATED APPLICATIONS

This application is a continuation of International Patent Application No. PCT/US2014/063473 filed Oct. 31, 2014, which claims the benefit of Provisional Patent Application No. 61/899,106 filed Nov. 1, 2013, both of which are hereby incorporated by reference.

FIELD OF THE INVENTION

The invention relates generally to an accommodating intraocular lens device and, more particularly, to an accommodating intraocular lens device configured for implantation in a lens chamber of a subject's eye.

BACKGROUND

Surgical procedures on the eye have been on the rise as technological advances permit for sophisticated interventions to address a wide variety of ophthalmic conditions. Patient acceptance has increased over the last twenty years as such procedures have proven to be generally safe and to produce results that significantly improve patient quality of life.

Cataract surgery remains one of the most common surgical procedures, with over 16 million cataract procedures being performed worldwide. It is expected that this number will continue to increase as average life expectancies continue to rise. Cataracts are typically treated by removing the crystalline lens from the eye and implanting an intraocular lens ("IOL") in its place. As conventional IOL devices are primarily focused for distance visions, they fail to correct for presbyopia and reading glasses are still required. Thus, while patients who undergo a standard IOL implantation no longer experience clouding from cataracts, they are unable to accommodate, or change focus from near to far, from far to near, and to distances in between.

Surgeries to correct refractive errors of the eye have also become extremely common, of which LASIK enjoys substantial popularity with over 700,000 procedures being performed per year. Given the high prevalence of refractive errors and the relative safety and effectiveness of this procedure, more and more people are expected to turn to LASIK or other surgical procedures over conventional eyeglasses or contact lens. Despite the success of LASIK in treating myopia, there remains an unmet need for an effective surgical intervention to correct for presbyopia, which cannot be treated by conventional LASIK procedures.

As nearly every cataract patient also suffers from presbyopia, there is convergence of market demands for the treatment of both these conditions. While there is a general acceptance among physicians and patients of having implantable intraocular lens in the treatment of cataracts, similar procedures to correct for presbyopia represent only 5% of the U.S. cataract market. There is therefore a need to address both ophthalmic cataracts and/or presbyopia in the growing aging population.

BRIEF SUMMARY

The intraocular lens (IOL) device described herein generally comprise two lens portions. In a preferred embodiment, a first lens portion provides most, if not all, of the accommodative power and a second base lens provides most, if not all, of the corrective refractive power that is needed by a particular patient. Because the first lens portion must provide an accommodative power, it must respond by either changing shape or by displacement along an optical axis in response to the contraction and relaxation of the ciliary muscles which control the eye's natural ability to accommodate. To that end, the first lens portion may be provided as an elastically deformable lens chamber that is filled with a fluid or gel. In contrast to the elastically deformable lens chamber, the base lens is configured to not readily deform or change its curvature in response to the radially compressive forces exerted on the circumferential edge. The transfer of the radially compressive forces onto the lens chamber may be accomplished by incorporating one or more of the following features in the IOL: (1) the opposing sides of the lens chamber having a reduced thickness as compared to the base lens, (2) a hinge disposed between the base lens and the peripheral portion, (3) the lens chamber being made of a material having a lower Young's modulus than the base lens, and/or (4) the base lens being made of a substantially rigid material.

In one embodiment, an intraocular lens (IOL) device is provided. The IOL comprises a first lens comprising a pair of opposing and deformable surfaces and a cavity defined therebetween, the first lens having a first lens diameter, a second lens having a second lens diameter, and a circumferential haptic having an outer peripheral edge, the circumferential haptic coupling the first lens and the second lens. A main IOL cavity is defined by the circumferential haptic, the first lens and the second lens. The IOL device is resiliently biased to an unaccommodated state being characterized by the IOL device having a first diameter $d_1$ in the absence of radial compressive forces exerted on the outer peripheral edge. The IOL device actuates to an accommodated state characterized by a second diameter $d_2$ in response to radial compressive forces exerted on the outer peripheral edge, wherein $d_1 > d_2$.

In accordance with a first aspect, the first lens is a biconvex lens.

In accordance with a second aspect, the cavity is fully enclosed.

In accordance with a third aspect, the IOL further comprises a gel in the cavity. The gel preferably has a refractive index of 1.46 or greater, preferably 1.48 or greater and most preferably 1.55 or greater. The gel preferably has a Young's modulus of 10 psi or less, preferably 5 psi or less, and more preferably 1 psi or less. In a particularly preferred embodiment, the gel has a Young's modulus of 0.5 psi or less, preferably 0.25 psi or less, and most preferably 0.01 psi or less. The gel preferably is a highly-branched polymer, preferably cross-linked silicone.

In accordance with a fourth aspect, the second lens is a one of a plano-convex lens, a bi-convex lens and a positive meniscus lens.

In accordance with a fifth aspect, the second lens is substantially more rigid than the first lens.

In accordance with a sixth aspect, the IOL further comprises a hinge disposed between the circumferential haptic and the second lens. In a preferred embodiment, in the presence of the compressive forces on the peripheral edge, the hinge directs a substantial portion of the compressive forces onto the first lens to cause a greater proportionate reduction in the first lens diameter to be reduced proportionately than in the second lens diameter.

In accordance with a seventh aspect, each of the opposing and deformable surfaces of the first lens has a thickness that is 50% or less of the second lens, preferably 25% or less of the second lens, and more preferably, 10% or less of the second lens.

In accordance with an eighth aspect, the IOL further comprises one or both of a plurality of apertures disposed on the circumferential haptic and a circumferential channel defined within the circumferential haptic. The plurality of apertures may be in fluid communication with the main IOL cavity. The plurality of apertures may be in fluid communication with both the circumferential channel and the main IOL cavity.

In accordance with a ninth aspect, the IOL device further comprises a plurality of raised bumps, wherein at least one of the plurality of raised bumps is positioned adjacent to each one of the plurality of apertures.

In accordance with a tenth aspect, the IOL device further comprises a plurality of troughs, at least one of the plurality of troughs extending radially inward from each one of the plurality of apertures to facilitate fluid flow into the apertures.

In accordance with an eleventh aspect, the circumferential haptic comprises a plurality of radial arms coupling the second lens, the plurality of radial arms defining apertures therebetween to permit fluid communication with the main cavity.

In accordance with a twelfth aspect, the circumferential haptic comprises a third circumferential cavity disposed peripherally of the main IOL cavity.

In accordance with a thirteenth aspect, the opposing surfaces of the first lens are displaced away from each other upon the application of a radial force along the circumferential haptic. The opposing surfaces comprises central and peripheral regions and a gradually increasing thickness profile from the peripheral to the central regions.

In another embodiment, an IOL is provided. The IOL comprises a first lens made of an elastic and deformable material having a first Young's modulus, a second lens in spaced relation to the first lens along a central optical axis and a circumferential portion encircling the first and second lens, the circumferential portion comprising an outer peripheral edge. At least one of a portion of the second lens and a portion of the circumferential portion is made of a material having a second Young's modulus. The first Young's modulus is less than the second Young's modulus.

In accordance with a first aspect, only the second lens is made of the material having the second Young's modulus.

In accordance with a second aspect, only the portion of the circumferential portion is made of the material having the second Young's modulus.

In accordance with a third aspect, the first Young's modulus is about 100 psi or less.

In accordance with a fourth aspect, the second Young's modulus is about 100 psi or greater.

In accordance with a fifth aspect, the second Young's modulus is about 150 psi or greater.

In accordance with a sixth aspect, the first lens comprises a pair of opposing and deformable surfaces and a cavity defined therebetween, the first lens having a first lens diameter and wherein a main IOL cavity is defined between the first lens, the second lens and the circumferential portion.

In accordance with a seventh aspect, the IOL further comprises a hinge disposed on the second lens outside of the active optical area.

In accordance with an eighth aspect, the first lens is comprised of two opposing surfaces which are displaced away from each other upon the application of a radial force along a peripheral edge. The two opposing surfaces each having central and peripheral regions, wherein the central region has a thickness that is at least 2 times, preferably at least three times, and most preferably at least four times greater than a thickness of the peripheral region.

In a further embodiment, an IOL is provided. The IOL comprises a first lens, a second lens in spaced relation to the first lens and a circumferential haptic coupling the first and second lens. The first lens comprises opposing sides and an enclosed cavity between the opposing sides. The opposing sides each have central and peripheral regions, the central region being disposed around an optical axis, the peripheral region being disposed around the central region. The central region is at least two times thicker than the peripheral region. The second lens in spaced relation to the first lens, the second lens having a thickness that is greater than either one of the opposing sides of the first lens. A circumferential haptic has an outer peripheral edge configured for engagement with a capsular bag of an eye when the IOL is implanted. A main IOL cavity is defined by the circumferential haptic, the first lens and the second lens.

In accordance with a first aspect, the central region is at least three times thicker than the peripheral region.

In accordance with a second aspect, the central region is at least four times thicker than the peripheral region.

In accordance with a third aspect, the enclosed cavity of the first lens comprises a gel having a first refractive index.

In accordance with a fourth aspect, the opposing sides of the first lens has a second refractive index that is less than the first refractive index of the gel.

In accordance with a fifth aspect, the gel is a vinyl-terminated phenyl siloxane.

In accordance with a sixth aspect, the gel has a Young's modulus of 0.25 psi or less, preferably 0.01 psi or less.

Other objects, features and advantages of the described preferred embodiments will become apparent to those skilled in the art from the following detailed description. It is to be understood, however, that the detailed description and specific examples, while indicating preferred embodiments of the present invention, are given by way of illustration and not limitation. Many changes and modifications within the scope of the present invention may be made without departing from the spirit thereof, and the invention includes all such modifications.

BRIEF DESCRIPTION OF THE DRAWINGS

Illustrative embodiments of the present disclosure are described herein with reference to the accompanying drawings, in which.

Like numerals refer to like parts throughout the several views of the drawings.

DETAILED DESCRIPTION OF THE PREFERRED EMBODIMENTS

Specific, non-limiting embodiments of the present invention will now be described with reference to the drawings. It should be understood that such embodiments are by way of example and are merely illustrative of but a small number of embodiments within the scope of the present invention. Various changes and modifications obvious to one skilled in the art to which the present invention pertains are deemed to be within the spirit, scope and contemplation of the present invention as further defined in the appended claims.

Figure 1A:
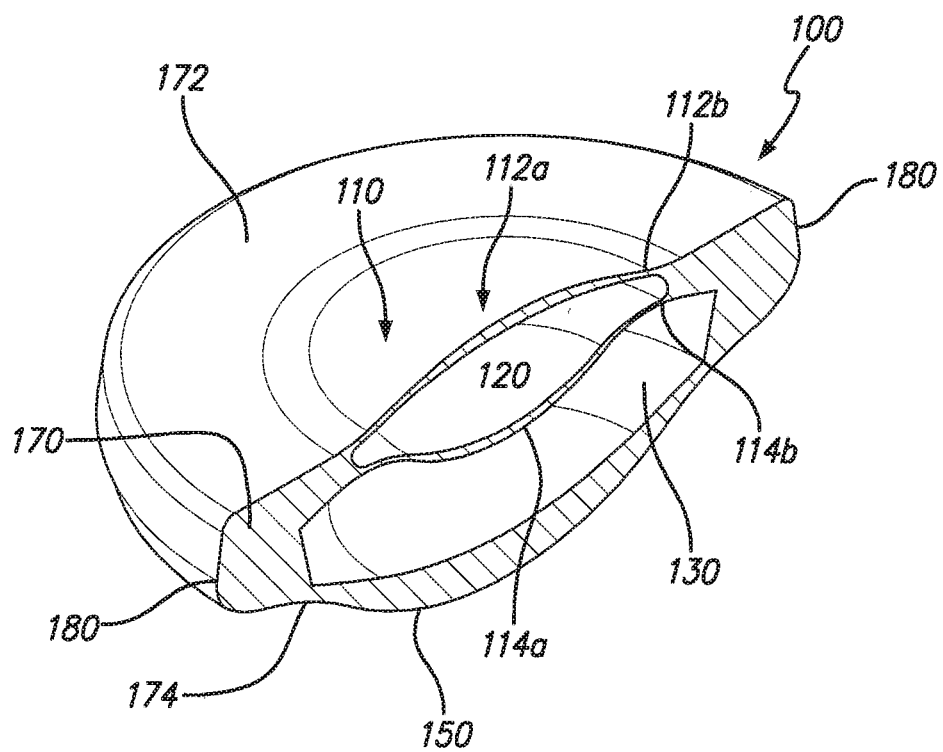
FIGS. 1A-1B are perspective and side cross-sectional views, respectively, of an embodiment of a dual-cavity IOL device.
Figure 1B:
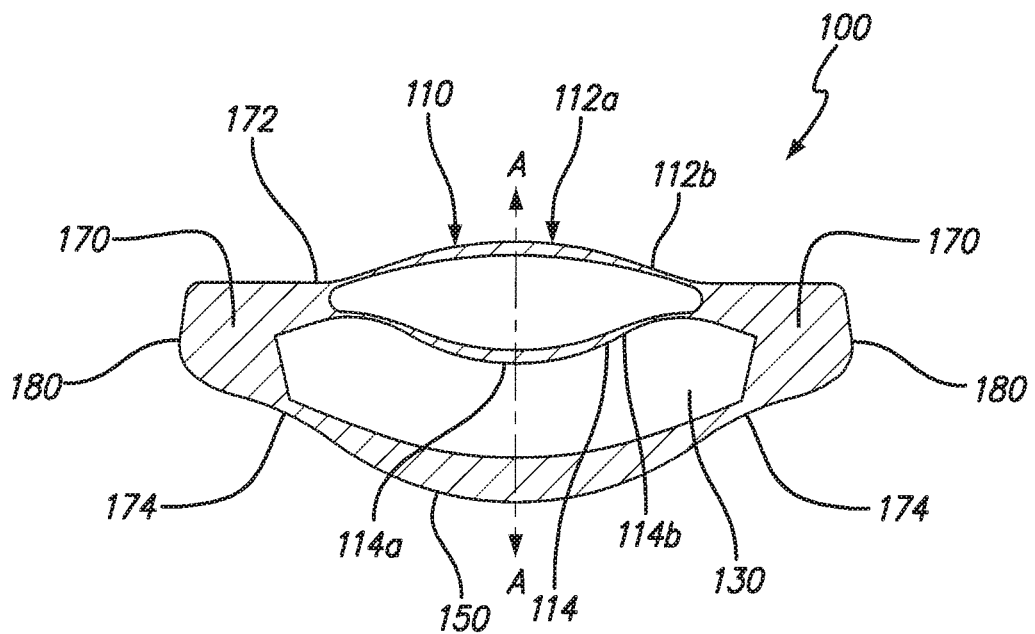

FIGS. 1A-1B depicts a basic structure of an embodiment of the accommodating intraocular lens (IOL) 100. The IOL 100 is depicted as comprising an elastically deformable lens chamber 110, a base lens 150, and a lens periphery 170 coupling the lens chamber 110 and the base lens 150. The elastically deformable lens chamber 110 provides most, if not all, of the accommodative power by deforming or changing in curvature in response to the radially compressive forces that are exerted onto the IOL 100 during accommodation. The base lens 150 provides most, if not all, of the corrective refractive power that is required by a particular patient and is not required to deform or change in shape or curvature. Thus, the lens chamber 110 and the base lens 150 cooperate to restore both a patient's vision and natural range of accommodation.

The lens chamber 110 is made of an elastically deformable material and comprises opposing sides 112 and 114 that are joined together at the periphery of the lens chamber 110 to define a bi-convex exterior shape and an internal enclosed cavity 120. Each of the opposing sides 112 and 114 comprise a central region 112a, 114a and a peripheral region 112b, 114b and a gradient of thickness that increases radially from the peripheral region 112b, 114b to the central region 112a, 114a. This thickness profile is intended to encourage deformation of the opposing sides 112, 114 away from one another and to permit the opposing sides to bulge and increase its curvature in opposing directions along an optical axis A-A without causing the membrane to buckle about the central region 112a, 114a. Thus, while the conventional wisdom suggests that a greater degree of deformation and outward bulging would be achieved with the opposite thickness profile (e.g., a thickness profile that decreases radially from the peripheral region 112b, 114b to the central region 112a, 114a), such a thickness profile is more likely to cause the lens chamber 110 to buckle or collapse inwardly about the central region 112a, 114a upon the application of a radially compressive force once implanted in a patient's eye. During accommodation, the application of radially compressive forces may cause an internal vacuum to develop inside the lens chamber 110, thereby causing the opposing sides 112, 114 to buckle inwardly.

Thus, in a particularly preferred embodiment, the opposing sides have a gradually increasing thickness from the peripheral regions 112b, 114b, to the central region 112a, 114a. In a preferred embodiment, the central region 112a, 114a, as measured along the optical axis A-A, has a thickness that is two times or more, preferably three times or more, and most preferably four times or more than the thickness of the peripheral region 112b, 114b, as measured just adjacent to the area where the opposing sides 112, 114 join at the peripheral region. In another preferred embodiment, the point of greatest thickness in the central region 112a, 114a and the point of least thickness in the peripheral regions 112b, 114b is characterized as having a thickness ratio of 2:1 or greater, preferably 3:1 or greater, and most preferably 4:1 or greater. In one embodiment, the central region 112a, 114a, as measured along the optical axis A-A, comprises an area of thickness that is about 100 microns, preferably about 200 microns, and the peripheral region 112b, 114b comprises an area of thickness that is about 50 microns as measured just adjacent to the area where the opposing sides 112, 114 join at the peripheral region. While the thickness profile is described in relation to FIGS. 1A-1B, it is understood that the same or a substantially similar thickness profile may be provided for all of the IOL devices depicted and described herein.

The base lens 150 is coupled to the lens chamber 110 via a lens periphery 170. The base lens 150 may be a positive lens that provides convergent power, such as a bi-convex, plano-convex or a positive meniscus lens. Alternatively, the base lens 150 may be a negative lens that provides divergent power, such as a bi-concave, plano-concave or a negative meniscus lens. The base lens 150 depicted in FIGS. 1A-1B is a positive meniscus lens.

The base lens 150 is preferably more rigid than the opposing sides 112, 114 of the lens chamber 110. The greater rigidity may be imparted by providing a base lens 150 having a thickness that is significantly greater than the thicknesses of the opposing sides 112, 114 of the lens chamber 110. Alternatively or in addition to providing a greater thickness, the base lens 150 may be made of a different or stiffer material having a higher elastic Young's modulus as compared to the lens chamber 110. The base lens 150 preferably does not substantially change its shape and curvature in response to the radially-compressive accommodative force applied onto the peripheral edge 180 of the lens periphery 170. Instead, the radially compressive accommodative forces are transferred onto the lens chamber 110 to cause the desired deforming changes.

Figure 9:
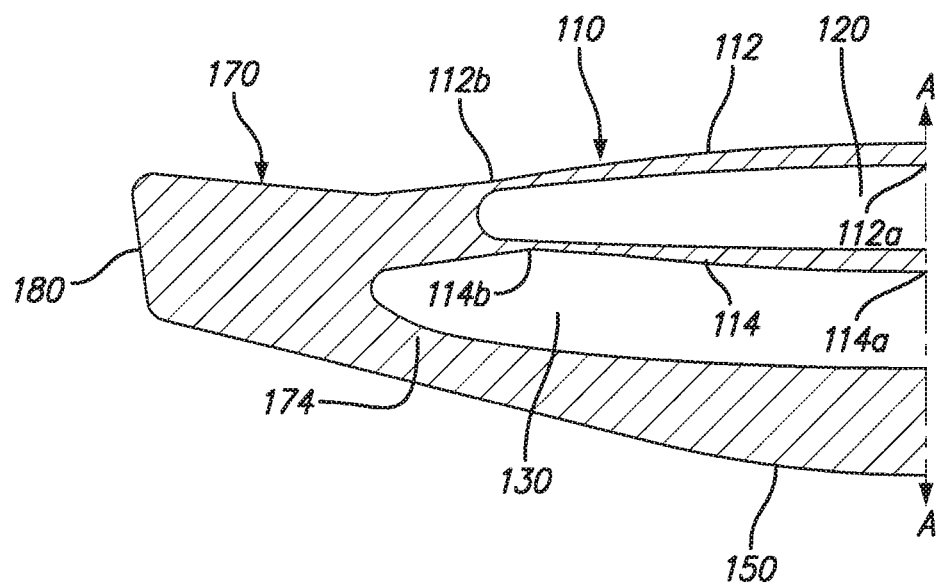
FIG. 9 is a partial cross-sectional view of an embodiment of the IOL device, cut away along the optical axis A-A.

In a preferred embodiment, the base lens 150 is substantially thicker than one of the opposing sides 112, 114 of the lens chamber 110, as measured along the optical axis A-A. In a preferred embodiment, the thickness of each one of the opposing sides 112, 114 of the lens chamber 110, as along the optical axis A-A depicted in FIGS. 1A-1B and 9, is less than ½, preferably less than ⅓, preferably less than ¼, and most preferably less than ⅕ of the thickness of the base lens 150 at the central optical axis A-A. Because the base lens 150 is substantially thicker than either one of the opposing sides 112, 114 of the lens chamber 110, the base lens 150 has an effective Young's modulus that is substantially greater than either one of the opposing sides 112, 114 of the lens chamber 110. While FIGS. 1A-1B and 9 depict the relative thickness of the opposing sides 112, 114 of the lens chamber 110 and the base lens 150 for IOL 100, it is understood that all of the IOL devices disclosed herein may have the same or similar thickness profile with respect to the lens chamber 110 and the base lens 150.

Figure 11A:
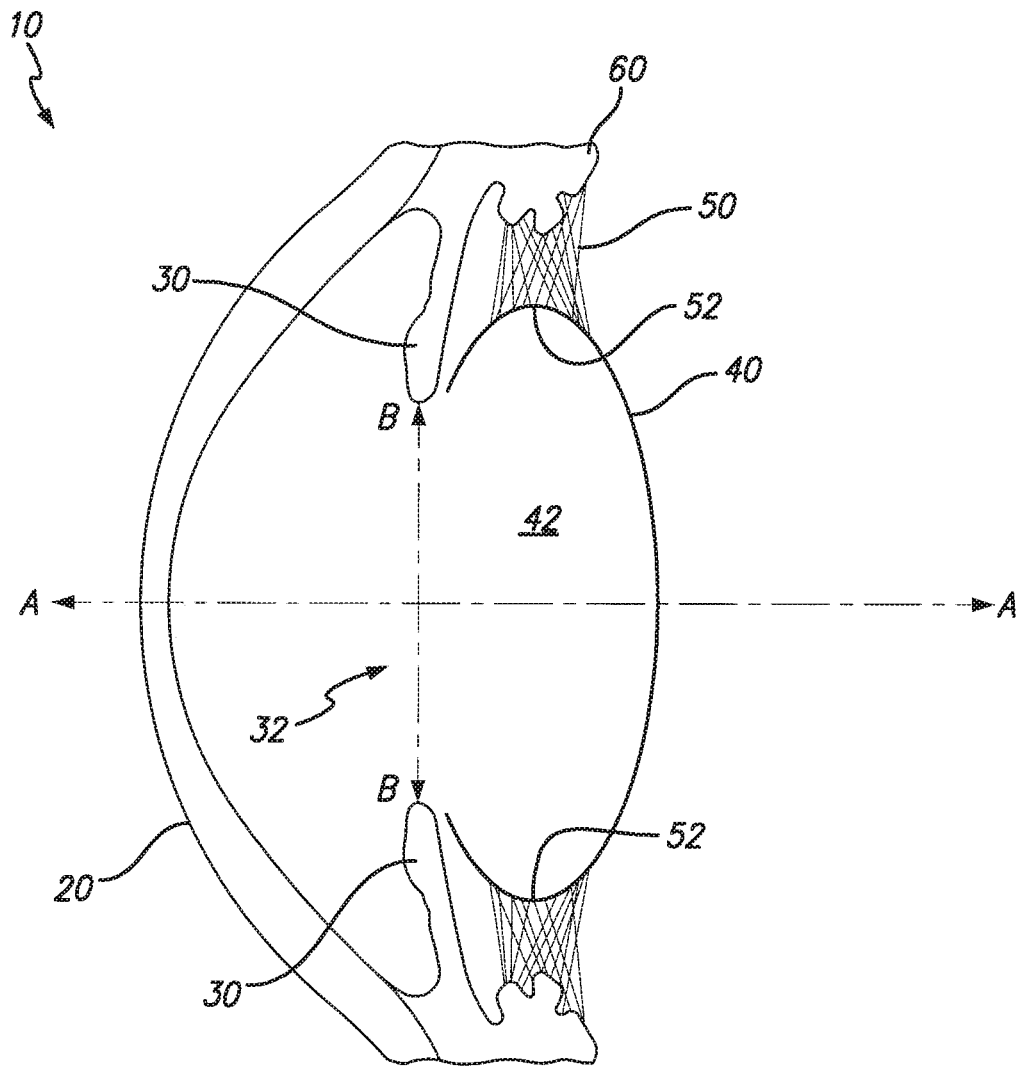
FIG. 11A depicts the human eye with the lens material removed following a capsulorhexis.
Figures 11B, 11C:
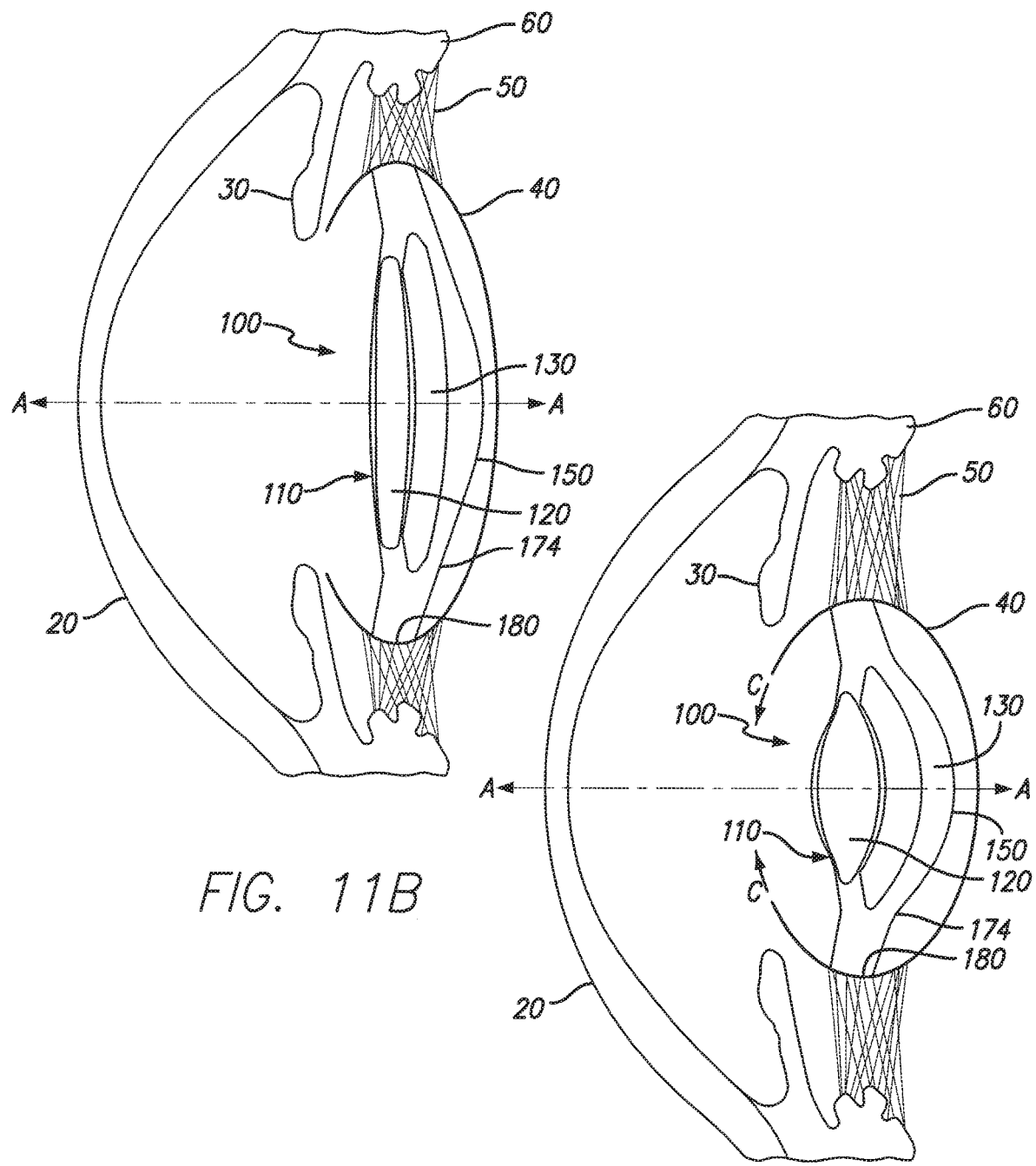
FIGS. 11B-11C depict the implanted IOL device in the unaccommodated and accommodated states, respectively.

The lens chamber 110 and the base lens 150 are coupled together by a lens periphery 170. The lens periphery 170 comprises a circumferential edge 180 configured to engage a circumferential region of the capsular bag of the eye. As depicted in FIGS. 11A-11C, the circumferential region 52 is where the capsular bag 40 is coupled to the zonules 50, generally at a location where the density of the zonules 50 is the greatest. The zonules 50, in turn, couple the capsular bag 40 to the ciliary muscles 60 which contract and relax to provide a range of accommodation. While FIGS. 11B and 11C depict a particularly preferred embodiment in which an IOL 100 is implanted with the lens chamber 110 being oriented anteriorly within the lens capsule 40 of the eye, it is understood that the IOL 100 may also be implanted with the lens chamber 110 being oriented posteriorly within the lens capsule 40 of the eye.

The lens periphery 170 comprises a radial portion 172 and a circumferential hinge 174 that cooperate together to transmit a significant portion, if not most, of the radially compressive forces exerted onto the circumferential edge 180 onto the lens chamber 110 and away from the base lens 150. Referring back to FIGS. 1A-1B, the radial portion 172 extends radially inwardly from the lens periphery 170 to the lens chamber 110 and the hinge 174 is disposed between the lens periphery 170 and the base lens 150. Both the radial portion 172 and the hinge 174 cooperate to maximize the extent to which the radially-compressive accommodative forces applied to the peripheral edge 180 are transmitted to the lens chamber 110. The greater the force transmitted to the lens chamber 110, the greater the deformation and change of curvature of the opposing sides 112, 114 of the lens chamber 110.

The lens periphery 170 may be solid and thickened as compared to the base lens 150, as depicted in FIGS. 1A-1B and 9. Alternatively, the lens periphery 170 may comprise a hollow space or a circumferential channel to reduce the delivery profile of the IOL, as depicted in FIGS. 2, 3A, 3B, 4, 6, 7, and 8. Because the IOL 100 is implanted into a relatively small incision size, it must be rolled up to assume a delivery profile that is at least as small as the incision size.

The circumferential hinge 174 is provided as a thinned or grooved area disposed in the lens periphery 170 and surrounding the base lens 150. The circumferential hinge 174 permits the lens periphery 170 to pivot radially inwardly towards the lens chamber 110 such that the radially compressive forces applied to the circumferential edge 180 are directed substantially along the radial portion 172 and applied to the lens chamber 110, as opposed to being applied to the base lens 150, which is configured to generally resist deformation (See FIG. 11C). Thus, the radial portion 172 is itself preferably sufficiently rigid in order to substantially transmit the radial compressive force onto the lens chamber 110. In a preferred embodiment, the hinge 174 is provided both peripherally and circumferentially around the base lens 150 as a thinned area or as a groove.

FIGS. 11B and 11C depicts the configuration of the IOL 100 in the absence of a radial compressive force applied to the circumferential peripheral edge 180 (FIG. 11B, an unaccommodated eye) and in the presence of a radial compressive force applied to the circumferential peripheral edge 180 (FIG. 11C, an accommodated eye) in which the peripheral edge 180 tilts in the direction C about the hinge 174, transmitting the radial compressive forces onto the lens chamber 110, and thereby causing the opposing sides 112, 114 of the lens chamber 110 to be displaced apart from one another and increase in curvature.

The features described herein which are intended to maximize the extent to which the radially compressive forces are transmitted to a lens chamber 110 and thus provide a large range of accommodation. The IOLs described herein may further be made of a material that does not resist deformation or is characterized as having a low Young's modulus. The IOLs may be made of a single material or, alternatively, different portions of the IOL may be made of different materials having differing Young's modulus (see FIGS. 10A-10B).

In one preferred embodiment, at least the opposing sides 112, 114 of the lens chamber 110 is made of a material of sufficient mechanical strength to withstand physical manipulation during implantation, but is of sufficiently low Young's modulus so as to minimize its resistance to deformation. In a preferred embodiment, the opposing sides 112, 114 of the lens chamber 110 is made of a polymer having a Young's modulus of 100 psi or less, preferably 75 psi or less, and most preferably 50 psi or less. In one preferred embodiment, the remaining portions of the IOL 100 (e.g., the base lens 150, the peripheral portion 170) has a Young's modulus that is greater than the Young's modulus of the walls 112, 114, of the lens chamber 110. The walls 112, 114 of the lens chamber 110 may be a polymer, preferably a silicone polymer and, more preferably a phenyl siloxane, such as a vinyl-terminated phenyl siloxane or a vinyl-terminated diphenyl siloxane. In order to impart sufficient mechanical strength, the polymer may be crosslinked, reinforced with fillers, or both. The fillers may be a resin or silica that have been functionalized to react with the polymer.

The opposing sides 112, 114 of the lens chamber 110 defines an enclosed cavity 120 that is filled with a fluid or gel having specific physical and chemical characteristics to enhance the range of refractive power provided by the IOL during accommodation. The fluid or gel is selected such that it cooperates with the walls 112, 114 of the lens chamber 110 in providing a sufficient range of accommodation of up to at least 3 diopters, preferably up to at least 5 diopters, preferably up to at least 10 diopters and most preferably up to at least 15 diopters. In a preferred embodiment, the enclosed cavity 120 is filled with the fluid or gel before implantation of the IOL 100 into the capsular bag 40 of the eye and, in a more preferred embodiment, the cavity 120 is filled with the fluid or gel in the manufacture of the IOL 100.

In one preferred embodiment the enclosed cavity 120 is filled with a fluid, such as a gas or a liquid, having low viscosity at room temperature and a high refractive index. In a preferred embodiment, the fluid is a liquid having a viscosity of 1,000 cP or less at 23° C. and a refractive index of at least 1.46, 1.47, 1.48, or 1.49. The fluid may be a polymer, preferably a silicone polymer, and more preferably a phenyl siloxane polymer, such as a vinyl-terminated phenyl siloxane polymer or a vinyl-terminated diphenyl siloxane polymer. Preferably, in embodiments where the fluid is made of a polymer, the polymer is preferably not crosslinked and that the polymer may be linear or branched.

Where the fluid is a vinyl-terminated phenyl siloxane polymer or diphenyl siloxane polymer, the vinyl groups may be reacted to form other moieties that do not form crosslinkages.

In accordance with one embodiment, fluid may be a polyphenyl ether ("PPE"), as described in U.S. Pat. No. 7,256,943, entitled "Variable Focus Liquid-Filled Lens Using Polyphenyl Ethers" to Teledyne Licensing, LLC, the entire contents of which are incorporated herein by reference as if set forth fully herein.

In accordance with another embodiment, the fluid may be a fluorinated polyphenyl ether ("FPPE"). FPPE has the unique advantage of providing tunability of the refractive index while being a chemically inert, biocompatible fluid with low permeability in many polymers. The tunability is provided by the increasing or decreasing the phenyl and fluoro content of the polymer. Increasing the phenyl content will effectively increase the refractive index of the FPPE, whereas increasing the fluoro content will decrease the refractive index of the FPPE while decreasing the permeability of the FPPE fluid through the walls 112, 114 of the lens chamber 110.

In another preferred embodiment, the enclosed cavity 120 is filled with a gel. The gel preferably has a refractive index of at least 1.46, 1.47, 1.48, or 1.49. The gel may also preferably have a young's modulus of 20 psi or less, 10 psi or less, 4 psi or less, 1 psi or less, 0.5 psi or less, 0.25 psi or less and 0.01 psi or less. In a preferred embodiment, the gel is a crosslinked polymer, preferably a crosslinked silicone polymer, and more preferably a crosslinked phenyl siloxane polymer, such a crosslinked vinyl-terminated phenyl siloxane polymer or a vinyl-terminated diphenylsiloxane polymer. Other optically clear polymer liquids or gels, in addition to siloxane polymers, may be used to fill the cavity 120 and such polymers may be branched, unbranched, crosslinked or uncrosslinked or any combination of the foregoing.

A gel has the advantages of being extended in molecular weight from being crosslinked, more self-adherent and also adherent to the walls or opposing sides or walls 112, 114 of the lens chamber 110 than most liquids. This makes a gel less likely to leak through the walls 112, 114 of the lens chamber 110. In order to obtain the combination of accommodative power with relatively small deformations in the curvature of the walls 112, 114 of the lens chamber 110, the gel is selected so as to have a high refractive index while being made of an optically clear material that is characterized as having a low Young's modulus. Thus, in a preferred embodiment, the gel has a refractive index of 1.46 or greater, preferably 1.47 or greater, 1.48 or greater and most preferably 1.49 or greater. At the same time, the gel preferably has a Young's modulus of 10 psi or less, preferably 5 psi or less, and more preferably 1 psi or less. In a particularly preferred embodiment, the gel has a Young's modulus of 0.5 psi or less, preferably 0.25 psi or less, and most preferably 0.01 psi or less. It is understood that at lower Young's modulus, the gel will present less resistance to deformation and thus the greater the deformation of the walls 112, 114 of the lens chamber 110 for a given unit of applied force.

In particularly preferred embodiment, the gel is a vinyl-terminated phenyl siloxane that is produced based on one of the four formulas provided as follows:

Formula 1:
100 parts 20-25 mole % vinyl terminated diphenylsiloxane-dimethylsiloxane copolymer (Gelest PDV 2335).
3 ppm platinum complex catalyst
0.35 pph of phenyl siloxane hydride crosslinker (Nusil XL-106)
Young's modulus of elasticity=0.0033 psi Formula 2:
100 parts 20-25 mole % vinyl terminated diphenylsiloxane-dimethylsiloxane copolymer (Gelest PDV 2335).
3 ppm platinum complex catalyst
0.4 pph of phenyl siloxane hydride crosslinker (Nusil XL-106)
Young's modulus of elasticity=0.0086 psi Formula 3:
100 parts 20-25 mole % vinyl terminated diphenylsiloxane-dimethylsiloxane copolymer (Gelest PDV 2335).
3 ppm platinum complex catalyst
0.5 pph of phenyl siloxane hydride crosslinker (Nusil XL-106)
Young's modulus of elasticity=0.0840 psi Formula 4:
100 parts 20-25 mole % vinyl terminated diphenylsiloxane-dimethylsiloxane copolymer (Gelest PDV 2335).
3 ppm platinum complex catalyst
0.6 pph of phenyl siloxane hydride crosslinker (Nusil XL-106)
Young's modulus of elasticity=2.6 psi The walls 112, 114 of the lens chamber 110 and the fluid or gel contained within the lens cavity 120 are preferably selected so as to prevent or reduce the likelihood of the fluid or gel migrating outside of the walls 112, 114 of the lens chamber 110. Thus, in a preferred embodiment, one or both of the walls 112, 114 of the lens chamber 110 and the fluid or gel is/are selected from biocompatible materials that optimize the resistance to permeability of the fluid or gel across the walls 112, 114 of the lens chamber 110.

One method of decreasing the permeability of the gel contained inside the cavity 120 across the walls 112, 114 of the lens chamber 110 is to provide a gel that is cross-linked. The degree of cross-linking, however, must be selected and controlled such that, on the one hand, the walls 112, 114 of the lens chamber 110 and the gel have a sufficiently low Young's modulus to minimize the resistance of the walls 112, 114 of the lens chamber 110 to deformation and, on the other hand, to minimize the permeation of the gel across the walls 112, 114 of the lens chamber 110. Thus, in a preferred embodiment, longer chain polymers that are lightly cross-linked, such as those used for silicone gels, starting with monomers having molecular weights that are greater than 35,000 daltons, preferably greater than 50,000 daltons and, most preferably, at least 70,000 daltons are desired.

In another preferred embodiment, a gel is used having low permeability extractables. Such gels may be formulated by using long chain polymers that are branched.

In a preferred embodiment, one or both of the lens chamber walls 112, 114 and the gel is made of homo- or co-polymers of phenyl-substituted silicones.

For the lens chamber walls 112, 114, the crosslinked homo- or co-polymers preferably have a diphenyl content of 5-25 mol %, preferably 10-20 mol % and more preferably 15-18 mol %. Alternatively, for the lens chamber walls 112, 114, the homo- or co-polymers preferably have a phenyl content of 10-50 mol %, preferably 20-40 mol %, and more preferably 30-36 mol %.

For the gel, the homo- or co-polymers preferably have a diphenyl content of 10-35 mol %, preferably 15-30 mol % and more preferably 20-25 mol %. Alternatively, for the gel, the homo- or co-polymers preferably have a phenyl content of 20-70 mol %, preferably 30-60 mol % and more preferably 40-50 mol %.

In a particularly preferred embodiment, the lens chamber walls 112, 114 are made of a crosslinked phenyl siloxane having a diphenyl content of about 15-18 mol % or a phenyl content of about 30-36 mol % and the gel is made of a phenyl siloxane having a diphenyl content of about 20-25 mol % or a phenyl content of about 40-50 mol %. The lens chamber walls 112, 114 are understood to be more crosslinked than the gel.

In a particularly preferred embodiment, the lens chamber walls 112, 114 are made of a vinyl-terminated phenyl siloxane, most preferably a crosslinked vinyl-terminated phenyl siloxane. Reinforcing agents, such as silica, may also be included in a range 10-70 mol %, preferably 20-60 mol % and most preferably 30-50 mol %.

The walls 112, 114 of the lens chamber 110 and the fluid or gel contained within the lens cavity 120 are also preferably selected so as to increase the range of accommodative power that is provided by the lens chamber 110. In one preferred embodiment, the walls 112, 114 of the lens chamber 110 are made of a material having a lower refractive index than the fluid or gel contained in the enclosed cavity. In one preferred embodiment, the refractive index of the lens walls 112, 114 of the chamber 110 is 1.38 and the refractive index of the gel or fluid is 1.49.

The differential refractive indices provided by the lens chamber walls 112, 114 and the gel or liquid contained within the chamber 120 may be provided by the differences in the materials or the composition of the materials used for the lens chamber walls 112, 114 and the gel or liquid.

In one embodiment, both the lens chamber walls 112, 114 and the gel or liquid is made of a phenyl siloxane having different diphenyl or phenyl content. In a preferred embodiment, the lens chamber walls 112, 114 has a diphenyl or phenyl content that is less than that for the gel or liquid. In another preferred embodiment, the walls 112, 114 of the lens chamber 110 may be made of a cross-linked vinyl-terminated phenyl siloxane having a diphenyl content of 15-18 mol % or a phenyl content of 30-36 mol % and the gel contained within the walls 112, 114 of the lens chamber 110 may be made of a vinyl-terminated phenyl-siloxane having a diphenyl content of 20-25 mol % or a phenyl content of 30-36 mol %.

In another embodiment, the differential refractive indices may be provided by providing a dimethyl siloxane for the lens chamber walls 112, 114 and the gel may be a phenyl siloxane having a high diphenyl or phenyl content. In a preferred embodiment, the diphenyl content is at least 20 mol %, at least 25 mol %, at least 30 mol %, at least 35 mol %, and at least 40 mol %. Alternatively, the phenyl content is at least 40 mol %, at least 50 mol %, at least 60 mol %, at least 70 mol %, and at least 80 mol %.

In a further embodiment, the differential refractive indices may be provided by a crosslinked fluoro siloxane, such as a 3,3,3-trifluoropropylmethyl siloxane and the gel may be a phenyl siloxane having a high diphenyl or phenyl content. In a preferred embodiment, the diphenyl content is at least 20 mol %, at least 25 mol %, at least 30 mol %, at least 35 mol %, and at least 40 mol %. Alternatively, the phenyl content is at least 40 mol %, at least 50 mol %, at least 60 mol %, at least 70 mol %, and at least 80 mol %.

Now turning back to FIGS. 1A-1B, a main cavity 130 is defined between the lens chamber 110, the base lens 150 and the lens periphery 170. The main cavity 130 is preferably filled with a fluid or gel. The fluid or gel in the main cavity 130 may be the same as the fluid or gel contained in the enclosed cavity 120. In a preferred embodiment, the fluid is a saline solution and the main cavity 130 is filled with the saline solution after implantation of the IOL in the capsular bag of the eye.

Filling the main cavity 130 after implantation of the IOL into the capsular bag will permit the IOL to take on a significantly smaller delivery profile such that the IOL may be rolled up and inserted through a relatively small incision. In a preferred embodiment, the incision size is less than 6 mm, preferably less than 5 mm, most preferably less than 4 mm and even most preferably less than 3 mm.

In embodiments where the main cavity 130 is filled with a fluid or gel after implantation, a valve (not shown) is preferably disposed on the IOL to permit injection of the fluid or gel into the main cavity 130 after implantation. The valve may be a one-way valve that permits injection of fluid or gel into the main cavity 130 but prevents the fluid or gel from exiting the main cavity 130. The valve is preferably disposed on the surface of the IOL that is facing in the anterior direction after it has been implanted in the eye. It is understood that the valve, however, is preferably not disposed on either one of the opposing sides 112, 114 so as to avoid disrupting the integrity of the lens chamber 110 which may house the same of different fluid or gel.

In a preferred embodiment, the fluids or gels in the respective enclosed cavity 120 and the main cavity 130 are completely segregated from one another. In one preferred embodiment, the enclosed cavity 120 and the main cavity 130 may have a different fluid and/or gel. In another preferred embodiment, one of the enclosed cavity 120 and the main cavity 130 may comprise one of a fluid or gel and the other one of the enclosed cavity 120 and the main cavity 130 may comprise the other one of a fluid or gel. In a preferred embodiment, there is no fluid exchanged between the enclosed cavity 120 and the main cavity 130.

The IOL 100 is intended to be implanted in a capsular bag 40 of the eye and centered about an optical axis A-A (See FIGS. 11A-11C). The lens chamber 110 and the base lens 150 are dimensioned to extend to or beyond the effective optical zone B-B as defined about the optical axis A-A of a patient's eye. The effective optical zone B-B is generally the largest possible opening through which light can enter the eye and thus is controlled by the largest effective diameter of the pupil 30 when completely dilated. This diameter is typically about 4-9 mm. Therefore, in a preferred embodiment, the diameters of the lens chamber 110 and the base lens 150 is preferably at least 4 mm, at least 5 mm, at least 6 mm, at least 7 mm, at least 8 mm and at least 9 mm.

As previously indicated, either one or both of the enclosed cavity 120 of the lens chamber 110 and/or the main cavity 130 is/are filled with a fluid or gel. The fluid may be a gas, a liquid. The fluid or gel preferably is characterized as having a sufficiently high refractive index such that the lens chamber 110 provides a range of accommodation in response to small changes in the curvature of the opposing sides 112, 114.

Because the IOL 100 is resiliently biased such that the opposing sides 112, 114 of the lens chamber 110 are substantially flat or have minimal curvature, small changes in the curvature of the opposing sides 112, 114 will lead to proportionately greater changes in the refractive power of the lens. Thus, the lens chamber 110, in combination with the base lens 150, can provide a change in the optical power of up to at least 3 diopters, preferably up to at least 5 diopters, preferably up to at least 10 diopters and most preferably up to 15 diopters in response to the accommodative forces (e.g., radially compressive forces) exerted on the implanted IOL.

Figure 2:
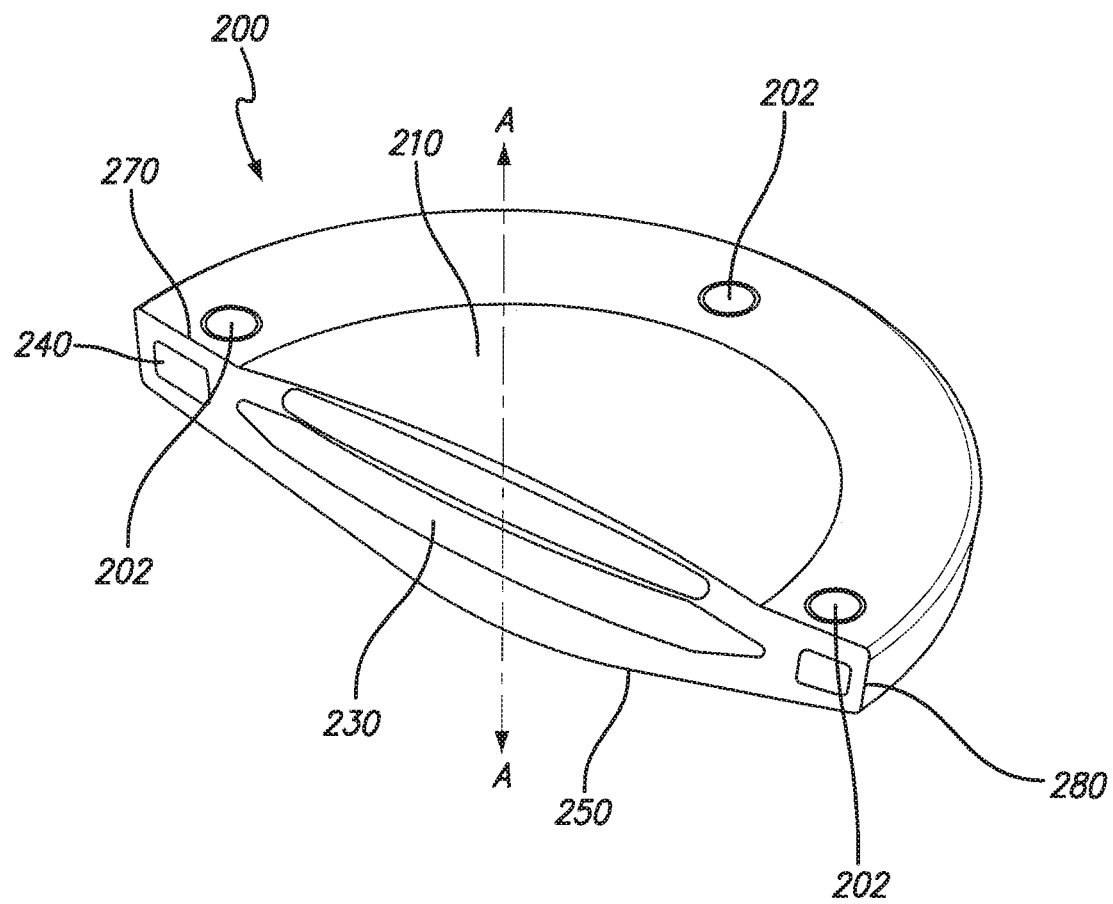
FIG. 2 is a perspective cross-sectional view of another embodiment of a dual-cavity IOL device having holes disposed on the top surface.

FIG. 2 depicts another embodiment of the IOL 200. The IOL 200 is similar in many respects with the IOL 100 of FIGS. 1A-1B in that it comprises a lens chamber 210, a base lens 250 and a lens periphery 270 joining the lens chamber 210 and the base lens 250. The lens periphery 270 further comprises a circumferential edge 280. The IOL 200 differs from IOL 100 in that IOL 200 comprises a plurality of holes 202 disposed circumferentially along the top surface of the IOL 200 and externally around the lens chamber 210 and a circumferential channel 240 disposed within the lens periphery 270. The holes 202 are intended to provide a fluid exchange channel between the circumferential channel 240, the main cavity 230 and the exterior of the IOL 200. The accommodative forces of the eye's capsular bag will cause the IOL 200 to radially expand and compress which, in turn, will cause the aqueous fluid to enter and exit the main cavity 230 through the holes 202. In a preferred embodiment, the holes 202 are disposed symmetrically about the top surface of the IOL 200.

Figure 3A:
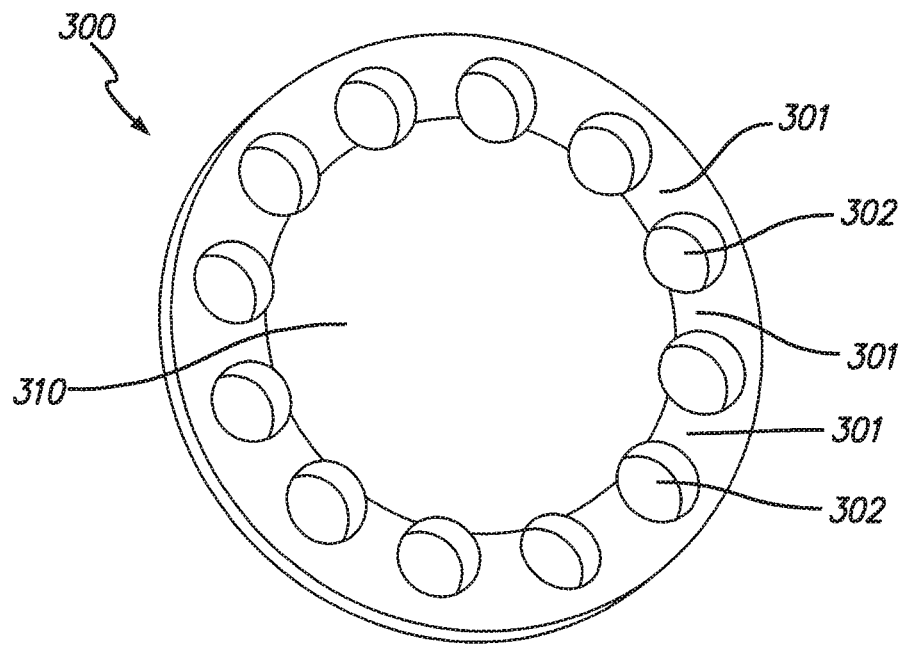
FIGS. 3A-3B are front and perspective cross-sectional views of another embodiment of a dual-cavity IOL device having through-holes disposed through the top and bottom surfaces in communication with the main cavity.
Figure 3B:
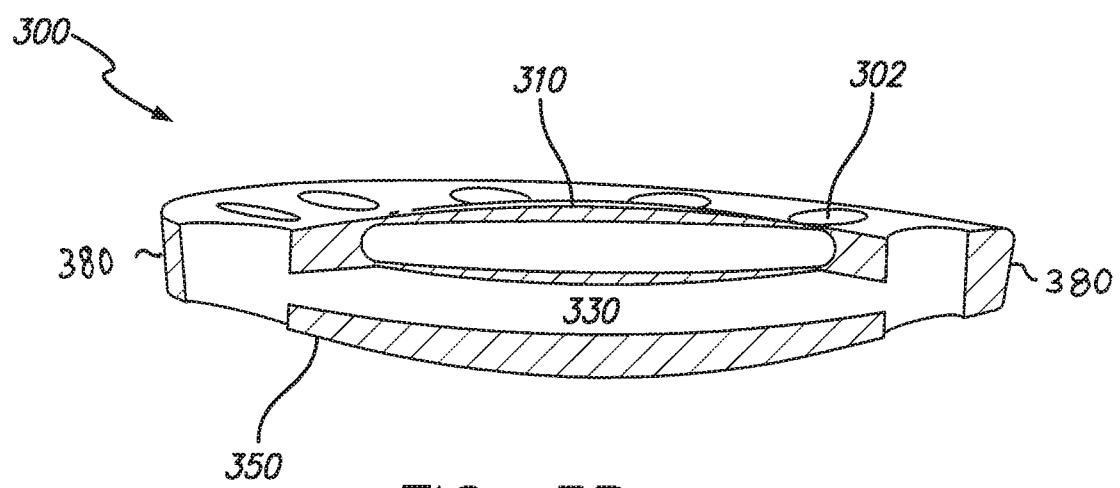

FIGS. 3A-3B depict another embodiment of the IOL 300 which comprises a plurality of through-holes 302 around the circumferential periphery of the IOL 300. The through-holes 302 differ from the holes 202 in FIG. 2 in that the through-holes are provided through both sides of the IOL 300 and the IOL 300 does not comprise a circumferential channel, whereas the holes 202 of the IOL 200 of FIG. 2 are only provided on the top surface of the IOL 200. The provision of through-holes 302 increase the efficiency with which the aqueous fluid fills and exits the main cavity 330.

Moreover, the through-holes 302 are dimensioned to be as large as can fit between the space between the circumferential edge 380 and the lens chamber 310. One advantage in the provision of numerous large through-holes 302 about the circumferential periphery is that it reduces the material bulk of the IOL 300 and permits it to take on a smaller delivery profile when it is folded and inserted into the capsular bag of the eye during implantation surgery. Thus, the IOL 300 will require a smaller incision for implantation into the capsular bag of the eye. It is understood, however, that the spacing 301 between the through-holes 302 must be sufficient to permit the transfer of force applied to the circumferential edge 380 onto the lens chamber 310. In a preferred embodiment, the spacing 301 is no more than ¼, preferably no more than ½, and most preferably no more than ¾ of the diameter of the through-holes 302.

Figure 4:
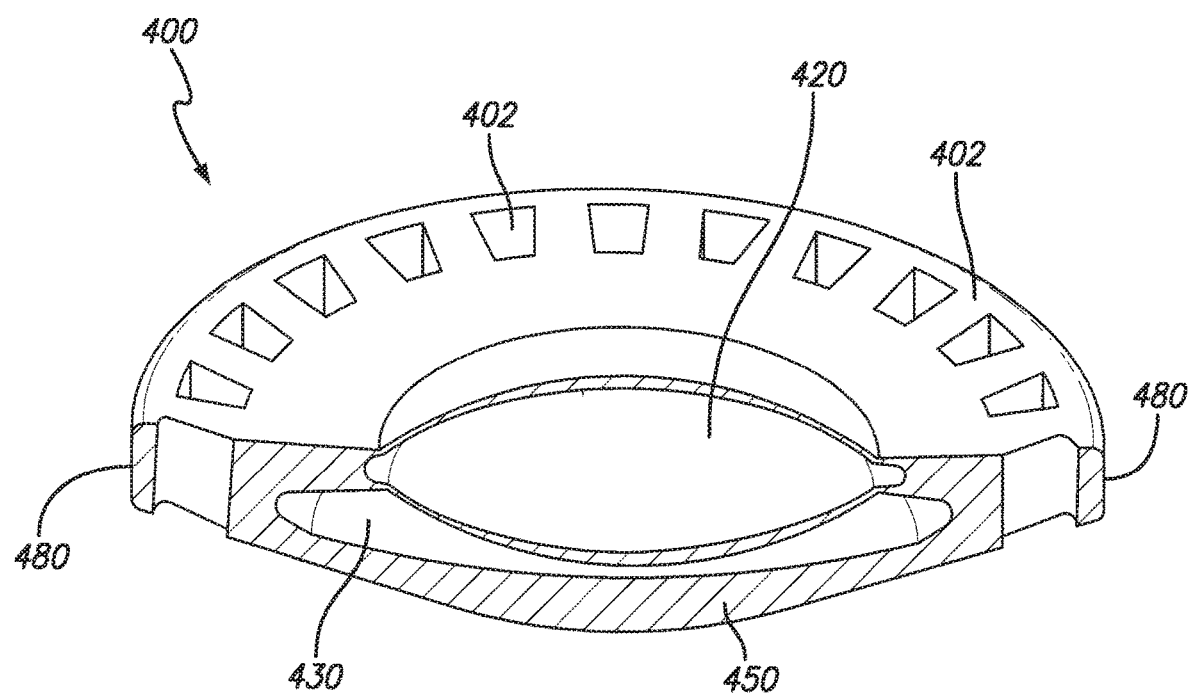
FIG. 4 is a perspective cross-sectional view of another embodiment of a dual-cavity IOL device having through-holes disposed through the top and bottom surfaces and which are not in fluid communication with the main cavity.

FIG. 4 depicts another embodiment of the IOL 400 also comprising through-holes 402, except that the through-holes 402 do not provide a fluid exchange between the main cavity 430 and the exterior of the IOL 400. The IOL 400 is thus similar to the IOL 100 of FIGS. 1A-1B in that a valve is required such that the main cavity 430 of the IOL 400 may be filled after implantation into the capsular bag of the eye. The main function of the through-holes 402 in this embodiment is to reduce the bulk of the IOL 400 so as to provide a smaller delivery profile. Thus, once implanted, the fluid or gel in the lens cavity 420 and the main cavity 430 remain contained and the IOL 400 does not permit for fluid exchange between the fluid in the exterior of the IOL 400 and the fluid or gel in the main cavity 430. FIG. 4 differs from the IOLs depicted in the preceding figures (FIGS. 1-3) in that it depicts the shape of the IOL 400 when a radial force is applied to the peripheral edge so as to cause a the opposing sides of the cavity 420 to bulge apart from one another. It is noted that the IOL 400 must be dimensioned such that the lower wall of the lens cavity 420 does not contact the base lens 450 within a range of the radial force that would be expected during the accommodation of the eye.

Figure 5A:
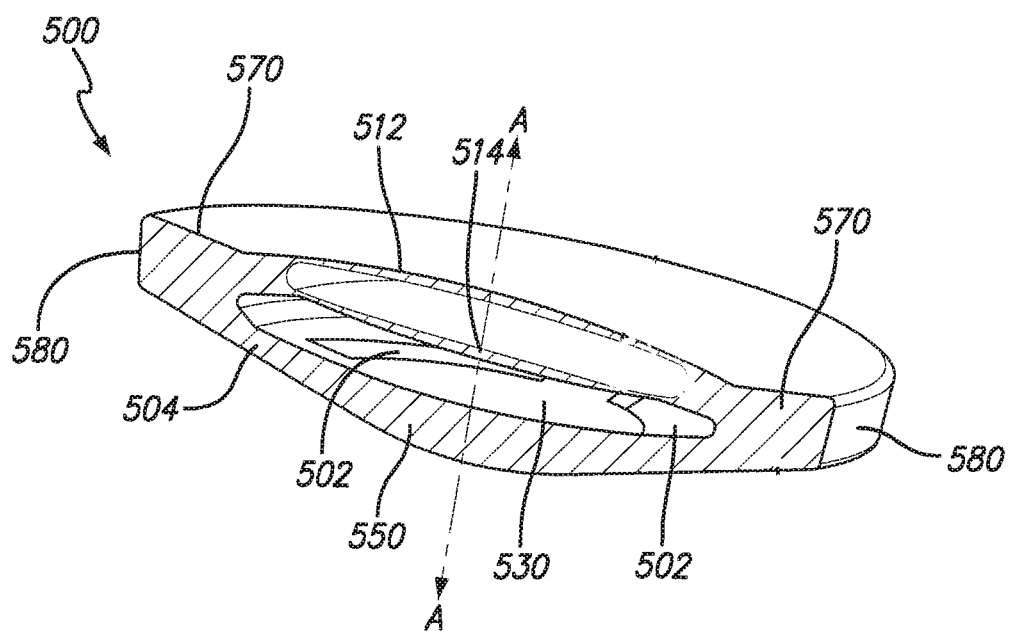
FIGS. 5A-5B are perspective cross-sectional views of another embodiment of a dual-cavity IOL device comprising arc-shaped cutouts on the bottom surface to provide a fluid communication with the main cavity.
Figure 5B:
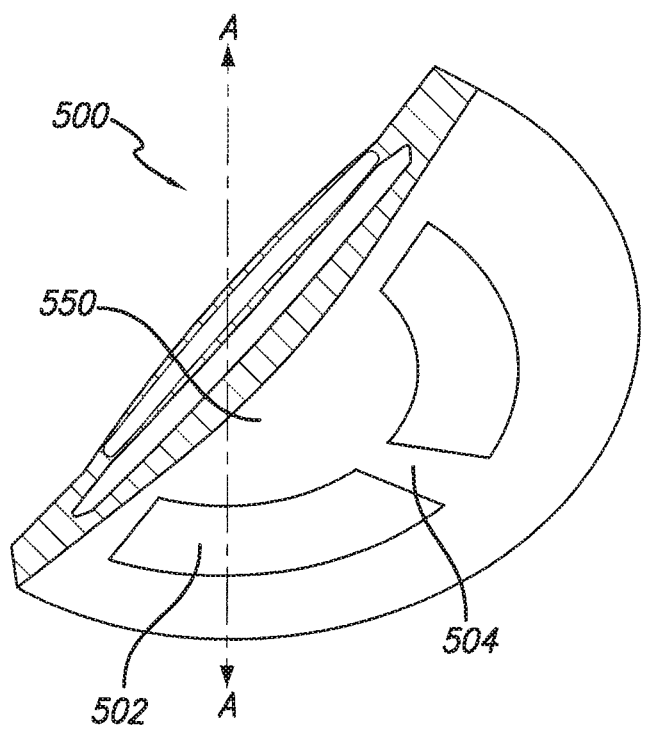

FIGS. 5A-5B depict yet a further embodiment of the IOL 500 which comprises a plurality of arc-shaped cutouts 502. The arc-shaped cutouts 502 are configured to function to provide a fluid exchange between the main cavity 530 and the exterior of the IOL 500. The IOL 500 comprises radial arms 504 between the arc-shaped cutouts 502 to couple and support the base lens 550 to the lens periphery 570. In a preferred embodiment, the radial arms 504 comprise a hinge between the peripheral portion 570 and the base lens 550 that permits the radial arms 504 to bend or rock inwardly upon application of a force upon the circumferential edge 580 so that the force is transferred to radially compressing the lens chamber 510. The hinge may simply be a groove or an area of reduced material thickness that is disposed either on the internal, external or both internal and external surfaces of the radial arms 504. As with the other IOLs described herein, the IOL 500 returns to a radially-expanded state in the absence of a force applied upon the circumferential edge 580. The IOL 500 is resiliently biased to a flatter configuration as shown in FIG. 5A in the absence of radially-compressive forces being exerted on the circumferential edge 580, as when the eye is unaccommodated. The IOL 500 is radially compressible to reduce the overall diameter of the lens chamber 110 and thus cause opposing sides 512, 514 of the lens chamber 510 to increase its curvature upon the application of a radially compressing force onto the circumferential edge 580, as when the eye is accommodated. See, e.g., FIG. 4.

Figure 6A:
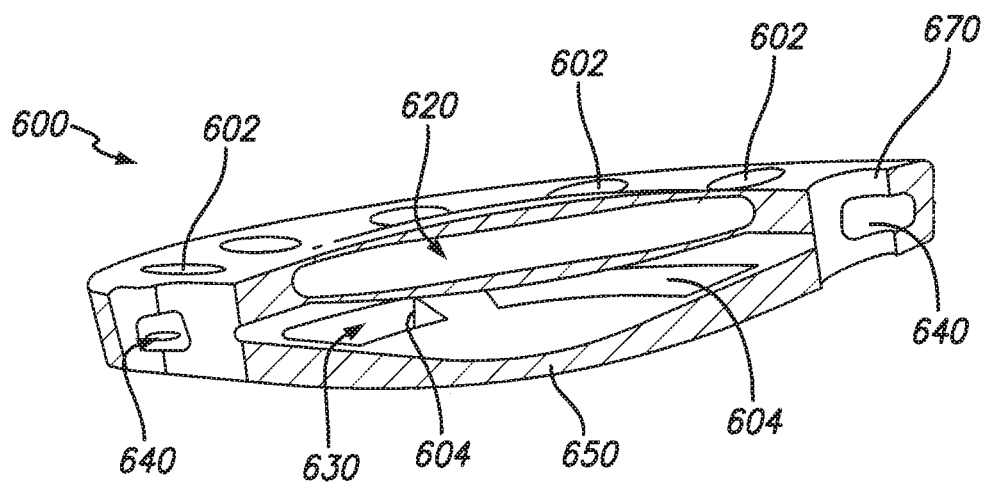
FIGS. 6A-6B are perspective cross-sectional and rear views of another embodiment of a dual-cavity IOL device comprising arch-shaped cutouts on the bottom surface and a plurality of peripheral through holes in communication with a circumferential channel.
Figure 6B:
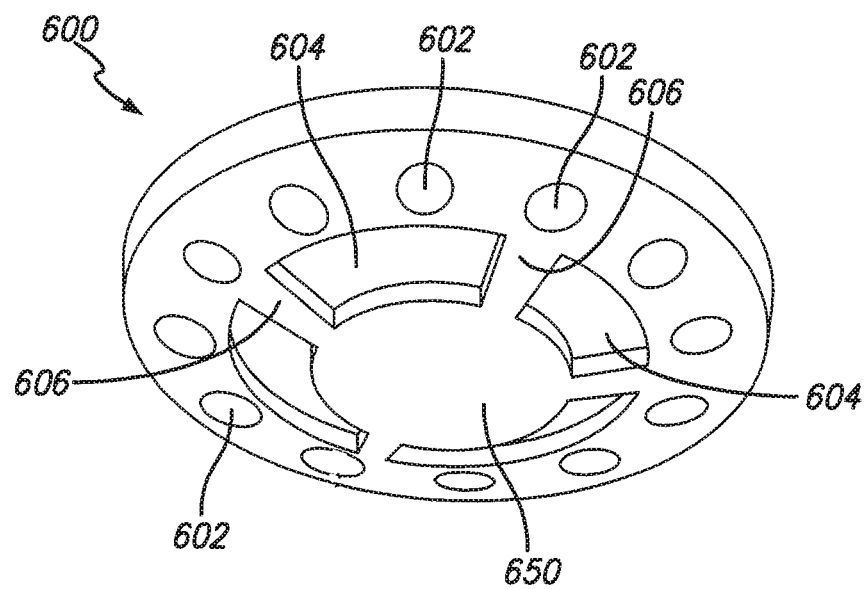
Figure 7A:
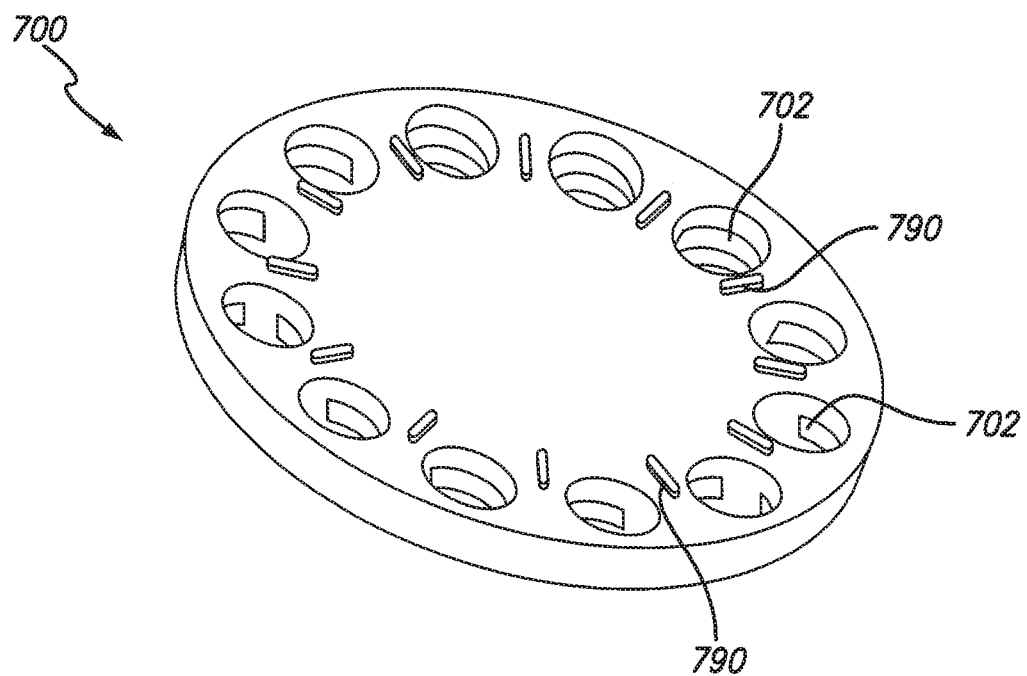
FIG. 7A-7B are top perspective and cross-sectional views of another embodiment of a dual-cavity IOL device comprising a plurality of raised protrusions adjacent through-holes which are in communication with the main cavity and circumferential channel.
Figure 7B:
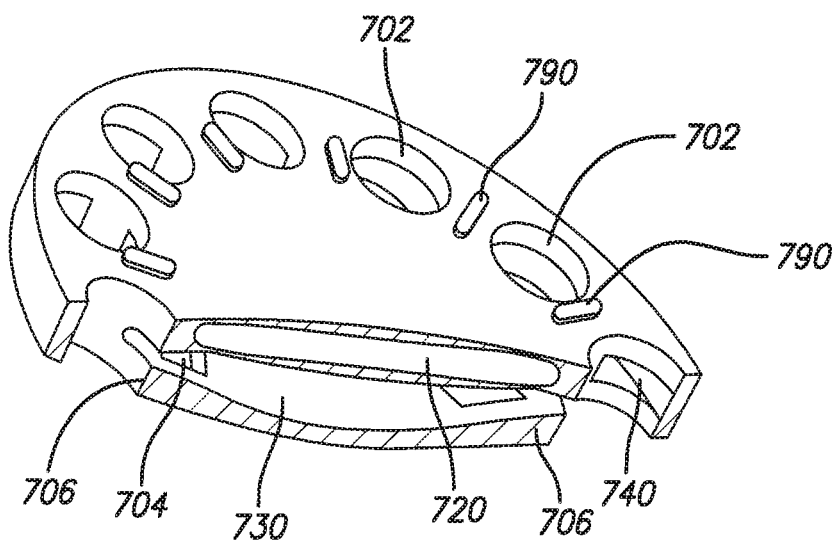
Figure 8A:
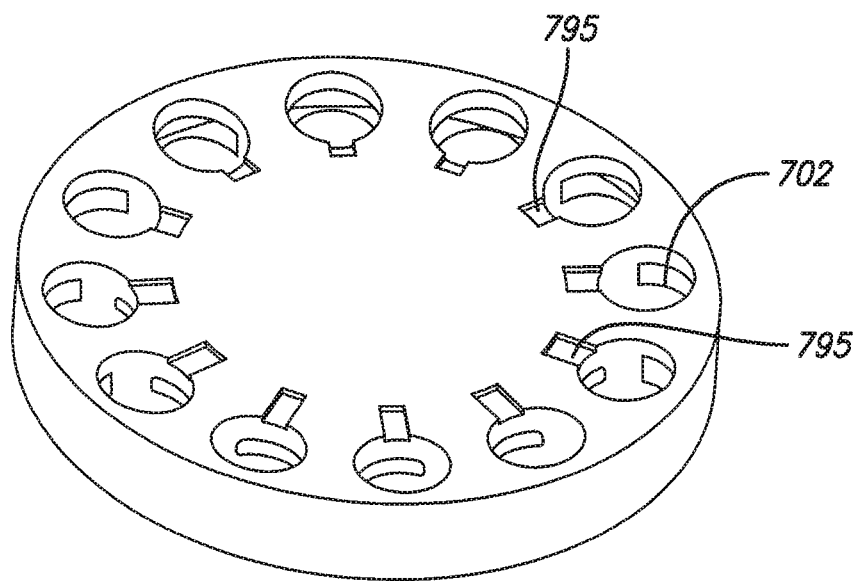
FIG. 8A-8B are top perspective and cross-sectional views of another embodiment of a dual-cavity IOL device comprising a plurality of troughs adjacent through-holes which are in communication with the main cavity and circumferential channel.
Figure 8B:
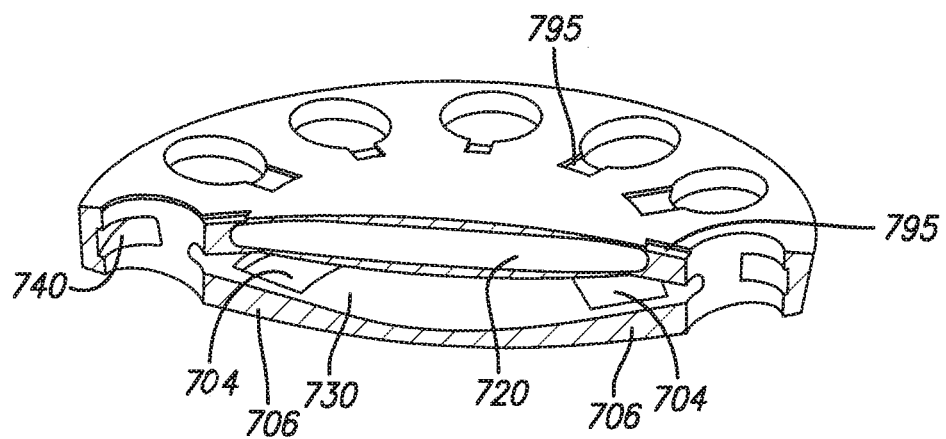

FIGS. 6A-6B depicts yet a further embodiment of the IOL 600 which comprises an internal circumferential channel 640 in addition to the enclosed cavity 620 and the main cavity 630. The circumferential through-holes 602 permit aqueous fluid flow into and out of the circumferential channel 640 and the arc-shaped cutouts 604 permit aqueous fluid flow into and out of the main cavity 630. Radial arms 606 couple the base lens 650 to the peripheral portion 670 and a hinge is disposed on the radial arm between the base lens 650 and the peripheral portion 670. Again, the presence of the internal circumferential channel 640 is intended to reduce the material bulk and thus to permit insertion of the IOL 600 through relatively smaller incisions.

The IOLs described herein are intended for implantation in a capsular bag of a patient's eye following performance of a capsulorhexis, in which a circular portion is removed from the anterior portion of the capsular bag.

FIG. 11A depicts the eye 10 following performance of a capsulhorexis and before implantation of an IOL. The eye 10 is depicted as comprising a cornea 20 through which the surgical incision is made to access the capsular bag 40. The diameter of the circular portion B-B removed from the capsular bag 40 depends upon each person's individual anatomy is typically in the range of from about 4 mm to about 9 mm. Here, the diameter 32 of the circular portion B-B removed from the capsular bag 40 corresponds roughly to the diameter of the pupil 30. Preferably, as much of the capsular bag 40 and its zonular connections 50 are maintained as possible. The zonules 50 couple the capsular bag 40 with the ciliary muscle 60 and transmit the accommodative forces to effectuate the curvature or shape changes of the capsular bag 40. Once the crystalline lens material is removed from the capsular bag 40, the IOL may be inserted and implanted such that the circumferential edge substantially engages the zonules 50 attached to the capsular bag 40. Additionally, the IOL is substantially centered along the optical axis A-A and engagement of the IOL with the zonules 50 is preferred to reduce the likelihood of decentration. In embodiments of the IOL comprising holes and through-holes, it is preferable that the holes and through-holes be located outside of the optical zone B-B. Moreover, the holes and through-holes should have rounded edges so as to prevent the perception of glare by the recipient.

FIGS. 7A-7B and 8A-8B depict an IOL 700 which is configured with raised protrusions 790 or troughs 795 adjacent to the through-holes 702 to create a space between the capsular bag and the through-holes 702 and to thereby ensure the free flow of the aqueous fluid in and out of the main cavity 730 and the circumferential channel 740.

The IOL 700 comprises three enclosed chambers: an enclosed lens chamber 720, a main cavity 730 and an internal circumferential channel 740. A plurality of circumferentially disposed through-holes 702 are sized to provide fluid exchange between both the main cavity 730 and the internal circumferential channel 740, on the one hand, and the exterior of the IOL 700, on the other hand. The fluid or gel in the lens chamber 720 remains contained within the lens chamber 720.

The IOL 700 further comprises arc-shaped cut-outs 704 and radial arms 706 disposed to couple the base lens 750 to the peripheral portion 770, in the same manner as depicted in FIGS. 6A-6B. The significant feature of IOL 700 is the presence of raised protrusions 790 (FIGS. 7A-7B) or troughs 795 (FIGS. 8A-8B) adjacent the through-holes 702. The raised protrusions 790 or troughs 795 are configured to ensure that the capsular bag does not form a seal over the through-holes 702 so as to impede or prevent the aqueous fluid from flowing freely in and out of the main cavity 730 and the circumferential channel 740.

As discussed above, the IOLs described herein are configured to transmit most, if not all, of the radially compressive forces exerted on the circumferential edge onto the lens chamber. In contrast to the elastically deformable lens chamber, the base lens is not configured to deform or change its curvature in response to the radially compressive forces exerted on the circumferential edge. The transfer of the radially compressive forces onto the lens chamber may be accomplished by incorporating one or more of the following features in the IOL: (1) the opposing sides of the lens chamber having a reduced thickness as compared to the base lens, (2) a hinge disposed between the base lens and the peripheral portion, (3) utilizing materials having different elastic moduli for the lens chamber and the base lens; and (4) the variation of refractive indices provided for the opposing sides of the lens chamber and the fluid or gel contained therein.

Figure 10A:
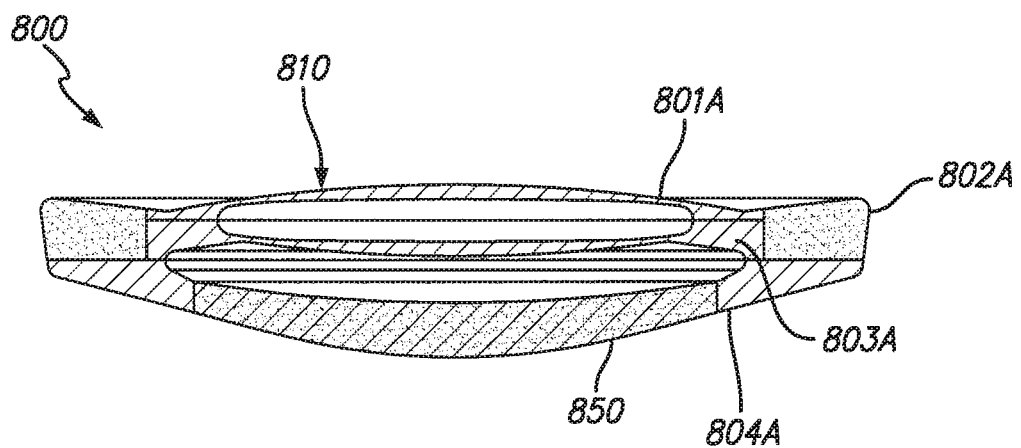
FIGS. 10A-10B are cross-sectional views of further embodiments of the IOL device.
Figure 10B:
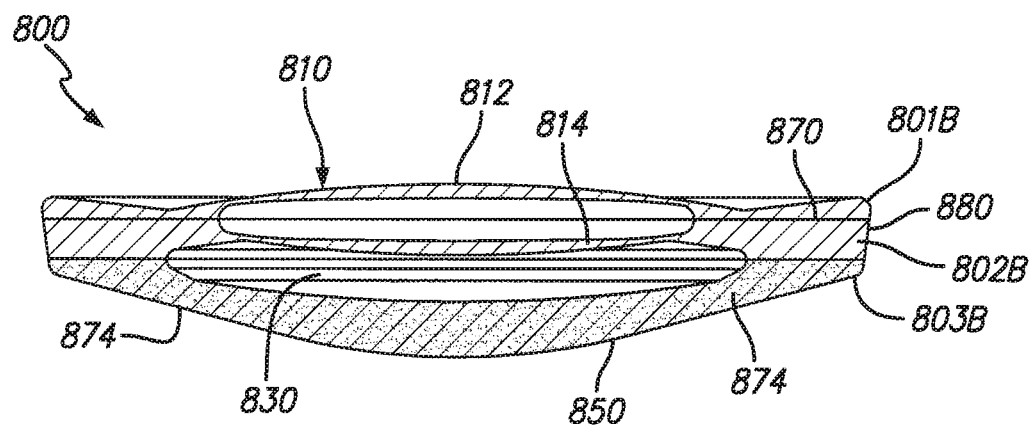

FIGS. 10A and 10B depict an IOL 800 which is constructed of at least two different elastomeric materials having different Young's modulus of elasticity, with at least the base lens 850 being made of a material having a higher Young's modulus than the lens chamber 810.

FIG. 10A depicts the IOL 800 as being constructed by assembling at least five (5) separately molded pieces, 801A, 802A, 803A, 804A, and 850. Thus, in addition to the two halves 801A, 803A of the lens chamber 810, The peripheral portion of the IOL 800 is provided in two ring portions 802A, 804A. The first ring portion 802A surrounding the lens chamber 810 has a higher elastic Young's modulus than the second ring portion 804A surrounding the base lens 850. In a preferred embodiment, the two halves 801A, 803A of the lens chamber 810 and the second ring portion 803A has a Young's modulus of 100 psi or less, preferably 75 psi or less, and most preferably 50 psi or less and the base lens 850 and the first ring portion 802 has a Young's modulus of more than 100 psi, preferably more than 250 psi, and most preferably more than 350 psi. In a particularly preferred embodiment, the Young's modulus of the first ring portion 802A may be up to 500 psi.

FIG. 10B depicts the IOL 800 as being constructed by assembling at least three (3) separately molded pieces 801B, 802B and 803B. The first lens chamber 810 and the surrounding peripheral portion is provided by assembling 801B and 802B and the base lens portion 850 and the surrounding peripheral portion is provided by assembling 803B to the underside of 802B. The assembled first lens chamber 810 and surrounding peripheral portion (801B, 802B) has a lower elastic Young's modulus than the base lens portion 850 and the surrounding peripheral portion (803B). In a preferred embodiment, portions 801B, 802B has a Young's modulus of 100 psi or less, preferably 75 psi or less, and most preferably 50 psi or less and the base lens portion 803B has a Young's modulus of more than 100 psi, preferably more than 250 psi and, most preferably, more than 350 psi. In a particularly preferred embodiment, the Young's modulus of the base lens portion 803B may be up to 500 psi.

The invention described and claimed herein is not to be limited in scope by the specific preferred embodiments disclosed herein, as these embodiments are intended as illustrations of several aspects of the invention. Indeed, various modifications of the invention in addition to those shown and described herein will become apparent to those skilled in the art from the foregoing description. Such modifications are also intended to fall within the scope of the appended claims.

The invention claimed is:

1. An intraocular lens (IOL) device comprising:
a first lens comprising a pair of opposing surfaces and a cavity defined therebetween, wherein the pair of opposing surfaces has at least one deformable surface;
a second lens;
a circumferential haptic having an outer peripheral edge, the circumferential haptic coupling the first lens and the second lens, wherein the circumferential haptic has an anterior surface and a posterior surface that are each configured to engage a lens capsule of a subject's eye, and wherein a peripheral axis parallel to a central optical axis extends from the anterior surface to the posterior surface, and wherein an uninterrupted anterior-posterior thickness along the peripheral axis and between the anterior and the posterior surfaces is greater than an anterior-posterior thickness of the second lens; and
a main IOL cavity disposed between the first lens and the second lens;
wherein the IOL device is resiliently biased to an unaccommodated state wherein the IOL device has a first diameter d1 in the absence of radial compressive forces exerted on the outer peripheral edge;
wherein the IOL device actuates to an accommodated state wherein the IOL has a second diameter d2 in response to the radial compressive forces exerted on the outer peripheral edge, wherein d1>d2; and
wherein the at least one deformable surface of the first lens is displaced away from the other opposing surface of the first lens upon application of a radial force along the circumferential haptic.

2. The IOL device of claim 1, wherein the first lens is a biconvex lens.

3. The IOL device of claim 1, wherein the cavity is fully enclosed.

4. The IOL device of claim 1, further comprising a gel in the cavity.

5. The IOL device of claim 4, wherein the gel has a refractive index of 1.46 or greater.

6. The IOL device of claim 4, wherein the gel has a Young's modulus of 10 psi or less.

7. The IOL device of claim 4, wherein the gel is a cross-linked vinyl-terminated phenyl siloxane polymer.

8. The IOL device of claim 1, wherein the second lens is one of a plano-convex lens, a bi-convex lens, and a positive meniscus lens.

9. The IOL device of claim 1, wherein the second lens is substantially more rigid than the first lens.

10. The IOL device of claim 1, further comprising a hinge disposed between the circumferential haptic and the second lens, wherein the hinge is thinner than portions of the circumferential haptic and the second lens adjacent to the hinge.

11. The IOL device of claim 10, wherein in the presence of the radial compressive forces on the outer peripheral edge, the hinge directs a substantial portion of the compressive forces onto the at least one deformable surface to cause a greater reduction in the first lens diameter than in the second lens diameter.

12. The IOL device of claim 1, wherein the deformable surface of the first lens has a thickness on the central optical axis that is 50% or less than a thickness of the second lens on the central optical axis.

13. The IOL device of claim 1, wherein the circumferential haptic comprises a plurality of radial arms coupling the second lens, the plurality of radial arms defining apertures therebetween to permit fluid communication with the main cavity.

14. The IOL device of claim 1, wherein the outer peripheral edge is continuous at a radially outermost edge and configured to engage the lens capsule of the subject's eye.

15. An intraocular lens (IOL) device comprising:
a first lens comprising an elastic and deformable material having a first Young's modulus, the first lens comprising a pair of opposing surfaces joined together at a periphery of the first lens to define a cavity therebetween;
a second lens in spaced relation to the first lens along a central optical axis;
a circumferential portion encircling the first and the second lens, the circumferential portion comprising an outer peripheral edge, an anterior surface, and a posterior surface, wherein a peripheral axis parallel to the central optical axis extends from the anterior surface to the posterior surface, and wherein a continuous expanse of material of the circumferential portion along the peripheral axis has an anterior-posterior thickness between the anterior and the posterior surfaces that is greater than an anterior-posterior thickness of the second lens along the central optical axis; and
a main IOL cavity defined between the first lens and the second lens;
wherein at least one of a portion of the second lens and a portion of the circumferential portion is made of a material having a second Young's modulus;
wherein the first Young's modulus is less than the second Young's modulus; and
wherein an application of a radial force applied along the outer peripheral edge is substantially transmitted to at least one of the opposing surfaces of the first lens via a flat radial portion, causing the at least one of the opposing surfaces of the first lens to be displaced away from the second lens.

16. The IOL device of claim 15, wherein only the second lens is made of the material having the second Young's modulus.

17. The IOL device of claim 15, wherein only the portion of the circumferential portion is made of the material having the second Young's modulus.

18. The IOL device of claim 15, wherein the first Young's modulus is 100 psi or less.

19. The IOL device of claim 15, wherein the second Young's modulus is 100 psi or greater.

20. The IOL device of claim 19, wherein the second Young's modulus is 150 psi or greater.

21. The IOL device of claim 15, further comprising a hinge disposed between the circumferential portion and the second lens, wherein the hinge is thinner than portions of the circumferential haptic and second lens adjacent to the hinge.

22. The IOL device of claim 15, wherein the at least one of the opposing surfaces comprises central and peripheral regions, the central region having a thickness that is at least 2 times greater than a thickness of the peripheral region.

23. The IOL device of claim 15, wherein the flat radial portion is proximate the peripheral region of the first lens and disposed radially outward relative to a radially outermost portion of the main IOL cavity.

24. An intraocular lens (IOL) device comprising:
a first lens comprising opposing surfaces and a cavity defined therebetween, wherein the opposing surfaces have at least one deformable surface;
a second lens;
a circumferential haptic having an outer peripheral edge that is continuous at a radially outermost edge and configured to engage a lens capsule of a subject's eye, the circumferential haptic coupling the first lens and the second lens, wherein the circumferential haptic has an anterior surface and a posterior surface disposed radially inward of the outer peripheral edge; and
a main IOL cavity disposed between the first lens and the second lens;
wherein the IOL device is resiliently biased to an unaccommodated state wherein the IOL device has a first diameter d1 in the absence of radial compressive forces exerted on the outer peripheral edge;
wherein the IOL device actuates to an accommodated state wherein the IOL device has a second diameter d2 in response to the radial compressive forces exerted on the outer peripheral edge, wherein d1>d2; and
wherein the at least one deformable surface of the first lens is displaced away from the other opposing surface of the first lens upon application of the radial compressive forces.

25. An intraocular lens (IOL) device comprising:
a first lens comprising an elastic and deformable material, the first lens comprising opposing surfaces joined together at a peripheral region of the first lens to define a cavity therebetween;
a second lens in spaced relation to the first lens along a central optical axis;
a main IOL cavity defined between the first lens and the second lens;
a circumferential portion encircling the first and the second lens, the circumferential portion comprising an outer peripheral edge and a flat radial portion proximate the peripheral region of the first lens, wherein the flat radial portion is disposed radially outward relative to a radially outermost portion of the main IOL cavity; and
wherein an application of a radial force applied along the outer peripheral edge is substantially transmitted to at least one of the opposing surfaces of the first lens via the flat radial portion, causing the at least one of the opposing surfaces of the first lens to be displaced away from the second lens.

26. The IOL device of claim 25, wherein at least a portion of the second lens and a portion of the circumferential portion is stiffer than a deformable portion of the first lens.

27. The IOL device of claim 25, wherein the opposing surfaces comprise at least one deformable surface.

28. The IOL device of claim 25, wherein the opposing surfaces comprise two surfaces configured to be displaced away from each other upon application of radially compressive forces.

\* \* \* \* \*